US011490808B2

(12) United States Patent
Noda

(10) Patent No.: US 11,490,808 B2
(45) Date of Patent: Nov. 8, 2022

(54) INFORMATION PROCESSING DEVICE AND INFORMATION PROCESSING METHOD

(71) Applicant: SONY CORPORATION, Tokyo (JP)

(72) Inventor: Takuro Noda, Tokyo (JP)

(73) Assignee: SONY CORPORATION, Tokyo (JP)

(*) Notice: Subject to any disclaimer, the term of this patent is extended or adjusted under 35 U.S.C. 154(b) by 257 days.

(21) Appl. No.: 16/631,901

(22) PCT Filed: May 22, 2018

(86) PCT No.: PCT/JP2018/019630
§ 371 (c)(1),
(2) Date: Jan. 17, 2020

(87) PCT Pub. No.: WO2019/021601
PCT Pub. Date: Jan. 31, 2019

(65) Prior Publication Data
US 2020/0154997 A1 May 21, 2020

(30) Foreign Application Priority Data
Jul. 27, 2017 (JP) .............................. JP2017-145346

(51) Int. Cl.
A61B 3/113 (2006.01)
A61B 3/00 (2006.01)

(52) U.S. Cl.
CPC ............ A61B 3/113 (2013.01); A61B 3/0008 (2013.01); A61B 3/0025 (2013.01); A61B 3/0041 (2013.01); A61B 3/0091 (2013.01)

(58) Field of Classification Search
CPC ..... A61B 3/113; A61B 3/0008; A61B 3/0025; A61B 3/0041; A61B 3/0091; G06F 3/013;
(Continued)

(56) References Cited

U.S. PATENT DOCUMENTS 5,848,295 A * 12/1998 Anderson ............. G06F 9/5016
719/312
9,886,237 B2 * 2/2018 Suzuki .................... B60R 11/02
(Continued)

FOREIGN PATENT DOCUMENTS

CN 104603673 A 5/2015
EP 2899585 A1 7/2015
(Continued)

OTHER PUBLICATIONS

International Search Report and Written Opinion of PCT Application No. PCT/JP2018/019630, dated Jul. 3, 2018, 09 pages of ISRWO.
Office Action for JP Patent Application No. 2019-532400, dated Apr. 26, 2022, 2 pages of Office Action and 2 pages of English Translation.

Primary Examiner — Mohammed A Hasan
(74) Attorney, Agent, or Firm — Chip Law Group

(57) ABSTRACT

Provided is an information processing device including an arithmetic processing unit that executes arithmetic processing related to calibration of detection of a sight line toward a display unit. The arithmetic processing unit determines calibration executability for each of both eyes based on acquired sight line data and uses only the sight line data of an eye for which calibration is determined to be executable when executing calibration for the eye.

19 Claims, 19 Drawing Sheets

(58) Field of Classification Search
CPC ........ G06F 3/0346; G06F 3/038; G06F 3/005; G06V 40/18
USPC ........................................................ 351/209
See application file for complete search history.

(56) References Cited

U.S. PATENT DOCUMENTS

| | | | |
|---|---|---|---|
| 10,431,060 B2* | 10/2019 | Saidi | G06F 1/163 |
| 2013/0208004 A1* | 8/2013 | Hamada | G02B 27/01 |
| | | | 345/633 |
| 2015/0286070 A1 | 10/2015 | Aikawa | |
| 2015/0288944 A1 | 10/2015 | Nistico et al. | |
| 2015/0365593 A1* | 12/2015 | Shinozaki | H04N 5/23264 |
| | | | 348/207.1 |

FOREIGN PATENT DOCUMENTS

| | | | | |
|---|---|---|---|---|
| JP | 2006-293909 A | 10/2006 | | |
| JP | 2007-136000 A | 6/2007 | | |
| JP | 2010-259605 A | 11/2010 | | |
| JP | 2016-502120 A | 1/2016 | | |
| JP | 2017-037329 A | 2/2017 | | |
| JP | 2017-102687 A | 6/2017 | | |
| JP | 2018-530798 A | 10/2018 | | |
| WO | WO-2006038784 A2 * | 4/2006 | ............ | G11B 19/02 |
| WO | 2014/033306 A1 | 3/2014 | | |
| WO | 2014/046206 A1 | 3/2014 | | |
| WO | WO-2017031089 A1 * | 2/2017 | ............ | A61B 3/113 |
| WO | 2017/094343 A1 | 6/2017 | | |

* cited by examiner

FIG.8
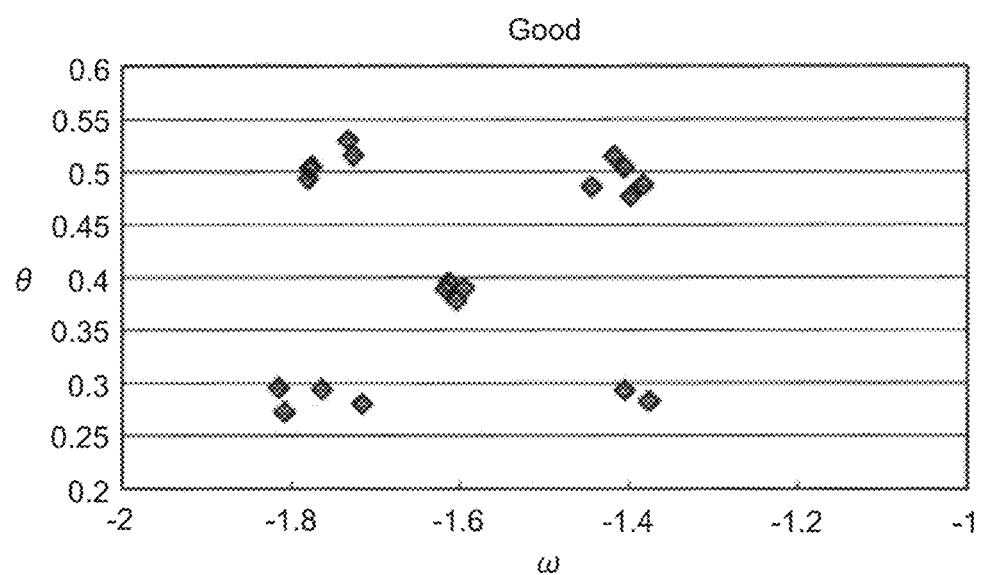
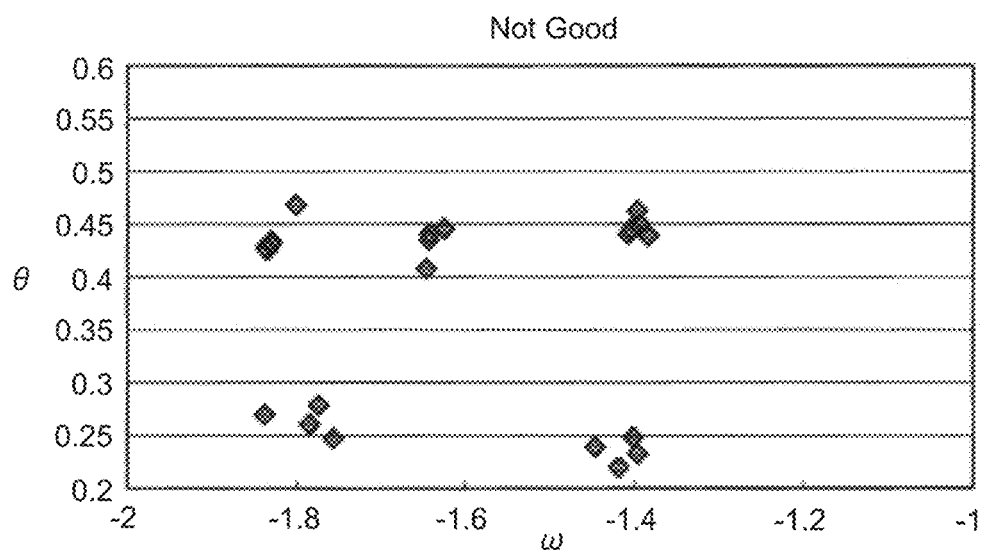

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2018/019630 filed on May 22, 2018, which claims priority benefit of Japanese Patent Application No. JP 2017-145346 filed in the Japan Patent Office on Jul. 27, 2017. Each of the above-referenced applications is hereby incorporated herein by reference in its entirety.

FIELD

The present disclosure relates to an information processing device, an information processing method, and a computer program.

BACKGROUND

A disclosed technology detects the sight line of a user toward a display surface on which various kinds of contents are displayed, and uses the detected sight line in various operations. For example, Patent Literature 1 discloses an image capturing apparatus configured to irradiate the eyeballs of a user gazing into a finder with light in an infrared band (infrared light) and capture reflected light from each eyeball by a detector to detect the sight line of the user toward a display surface on which a see-through image is displayed and use the detected sight line in automatic focusing (auto focus or AF).

CITATION LIST

Patent Literature

Patent Literature 1: JP H5-333259 A

SUMMARY

Technical Problem

However, when one of the eyes of a user does not function normally, it is difficult to correctly detect the sight line of the user by a method disclosed in Patent Literature 1. In addition, it is expected that the accuracy of sight line detection decreases when large difference occurs between detection results of sight line data on the right and left eyes.

Thus, the present disclosure discloses an information processing device and an information processing method that are novel, modified, and capable of performing sight line detection at higher accuracy.

Solution to Problem

According to the present disclosure, an information processing device is provided that includes an arithmetic processing unit configured to execute arithmetic processing related to calibration of detection of a sight line toward a display unit, wherein the arithmetic processing unit determines calibration executability for each of both eyes based on acquired sight line data and uses only the sight line data of an eye for which calibration is determined to be executable when executing calibration for the eye.

Moreover, according to the present disclosure, an information processing method is provided that includes executing, by a processor, arithmetic processing related to calibration of detection of a sight line toward a display unit, wherein the executing arithmetic processing further includes determining calibration executability for each of both eyes based on acquired sight line data and using only the sight line data of an eye for which calibration is determined to be executable when executing calibration for the eye.

Moreover, according to the present disclosure, a computer program is provided that causes a computer to function as an information processing device comprising an arithmetic processing unit configured to execute arithmetic processing related to calibration of detection of a sight line toward a display unit, wherein the arithmetic processing unit determines calibration executability for each of both eyes based on acquired sight line data and uses only the sight line data of an eye for which calibration is determined to be executable when executing calibration for the eye.

Advantageous Effects of Invention

As described above, according to the present disclosure, it is possible to perform sight line detection at higher accuracy by removing influence of one of the eyes that could cause decrease in accuracy.

The above-described effect is not necessarily restrictive, but any effect described in the present specification or any other effect understandable from the present specification may be achieved together with or in place of the above-described effect.

BRIEF DESCRIPTION OF DRAWINGS

FIG. 8 is a graph illustrating an exemplary result of evaluation of optical axis variance according to the embodiment.

DESCRIPTION OF EMBODIMENTS

Figure 1:
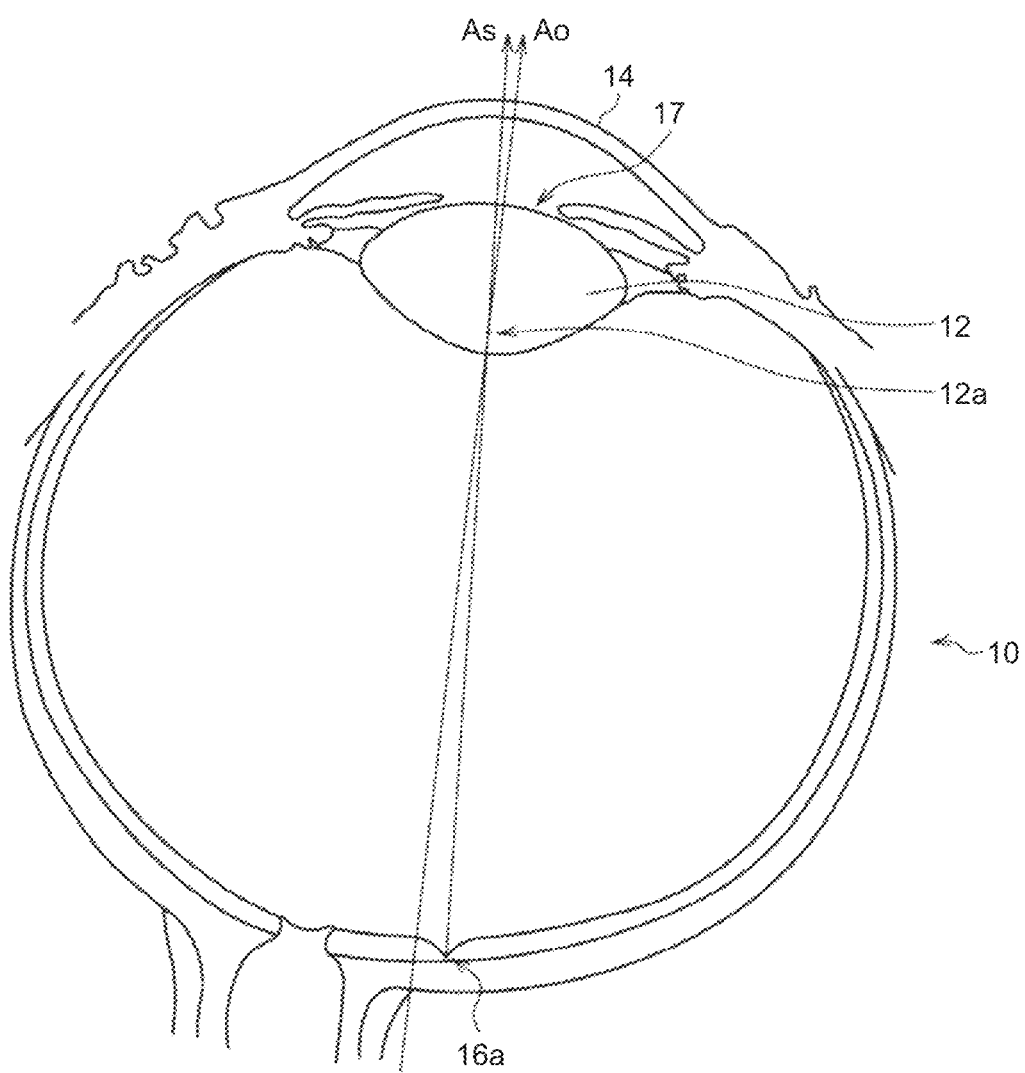
FIG. 1 is an explanatory diagram illustrating the structure of an eyeball.

Preferable embodiments of the present disclosure will be described below in detail with reference to the accompanying drawings. In the present specification and drawings, components having functional configurations identical to each other in effect are denoted by an identical reference sign, and duplicate description thereof are omitted.

Description will be made in the following order.
1. First Embodiment
1.1. Overview
1.2. Hardware configuration of display device
1.3. Functional configuration
1.4. Calibration processing
1.5. Calibration processing process
1.6. Display control based on calibration execution result
2. Second Embodiment
2.1. Overview
2.2. Characteristics of transparent member
3. Exemplary hardware configuration
4. Conclusion

1. FIRST EMBODIMENT

<<1.1. Overview>>

The following first describes overview of an information processing device according to a first embodiment of the present disclosure. FIG. 1 is an explanatory diagram illustrating the structure of an eyeball.

The information processing device according to the present embodiment performs calibration to improve the accuracy of sight line detection when the sight line of a user toward a display is to be detected. The information processing device according to the present embodiment detects the sight line of the user by, for example, a pupil cornea reflection method. The pupil cornea reflection method irradiates an eyeball of the user with light from a light source, detects reflected light of the light at the cornea surface and the position of the pupil, and estimates the direction of the sight line.

As illustrated in FIG. 1, the sight line of the user is aligned with a visual axis $A_s$ connecting a nodal point 12a at the center of the back surface of a lens 12 of an eyeball 10 and a central fovea 16a. The direction of the sight line estimated by the pupil cornea reflection method is aligned with an optical axis $A_O$ on the normal line of a cornea 14 passing through the center of a pupil 17. The visual axis $A_s$ and the optical axis $A_O$ are offset from each other and typically tilted from each other at 4° to 8° approximately, depending on the individual. When the offset is large, the accuracy of the sight line detection decreases, and thus calibration is performed to correct the offset.

The calibration is performed through procedures described below.

(Procedure 1) Estimate the optical axis when a point (hereinafter also referred to as "gaze point") in the visual field is gazed at.

(Procedure 2) Measure a difference between a gaze point vector from the center of cornea curvature to the gaze point and the vector of the estimated optical axis (Procedure 3) Estimate a visual axis from the optical axis when an optional point is gazed at based on the difference measured in (Procedure 2)

Since the eyeball 10 is rotated through pulling by muscles, roll rotation is performed depending on the gaze direction. Accordingly, calibration parameters differ with the orientation of the eyeball 10. Thus, the parameters are typically acquired for a plurality of gaze points (for example, five points to nine points) in the visual field.

In such calibration, error occurs to detection of reflected light at the pupil surface and estimation of the optical axis. The accuracy of the sight line detection can be improved by reducing variance of the error. Thus, the information processing device according to the present embodiment performs calibration to reduce error variance as described above.

In typical calibration, processing is executed by using sight line data of both eyes. However, as described above, for example, when one of the eyes does not function normally, it is expected that the sight line detection is difficult to perform and the accuracy of the sight line detection significantly decreases. Thus, it is one characteristic of the information processing device according to the present embodiment to determine calibration executability for each eye and use only sight line data of an eye for which calibration is determined to be executable when executing the calibration for the eye.

Figure 2:
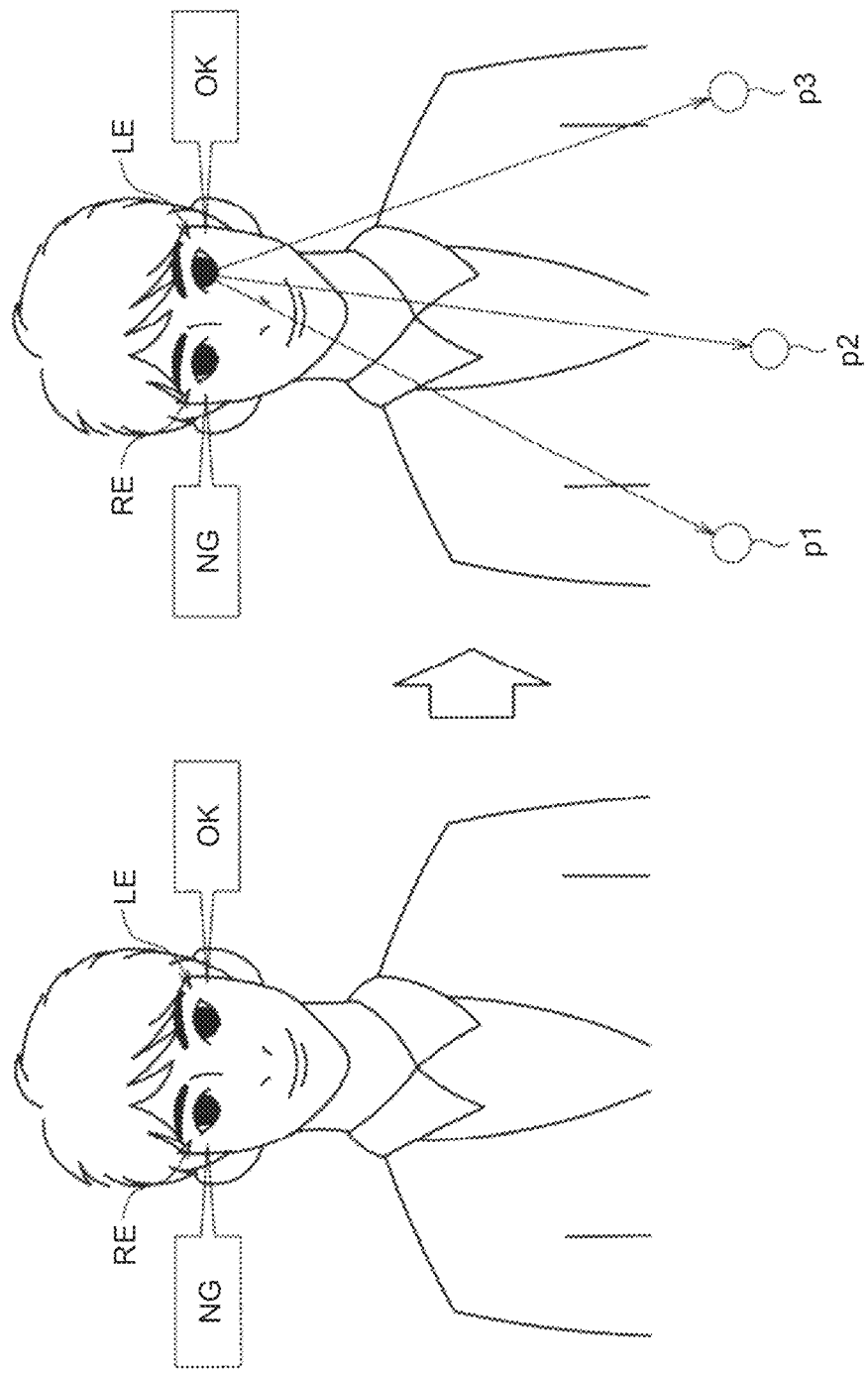
FIG. 2 is a diagram for describing an overview of a first embodiment according to the present disclosure.

FIG. 2 is a diagram for describing an overview of the present embodiment. FIG. 2 illustrates a situation in which a left eye LE of the user functions normally but a right eye RE thereof does not function normally. Examples of this situation include a case in which the right eye RE of the user is an artificial eye and a case in which strabismus is observed for the right eye RE.

In this case, the information processing device according to the present embodiment determines calibration executability for each of the left eye LE and the right eye RE, and uses only sight line data of the left eye LE for which calibration is determined to be executable when executing the calibration for the left eye LE. In addition, the information processing device according to the present embodiment can perform the sight line detection by using only sight line data of the left eye LE for which the calibration has been executed. In the example illustrated in FIG. 2, the information processing device acquires only sight line data of the left eye LE for which the calibration has been executed, and detects the sight line of the user toward each of Points P1 to P3.

According to the above-described function of the information processing device according to the present embodiment, it is possible to detect the sight line of the user even when one of the eyes does not function normally. In addition, according to the information processing device according to the present embodiment, it is possible to perform sight line detection at higher accuracy by removing influence of an eye that could cause accuracy decrease.

<<1.2. Hardware Configuration of Display Device>>

Figure 3:
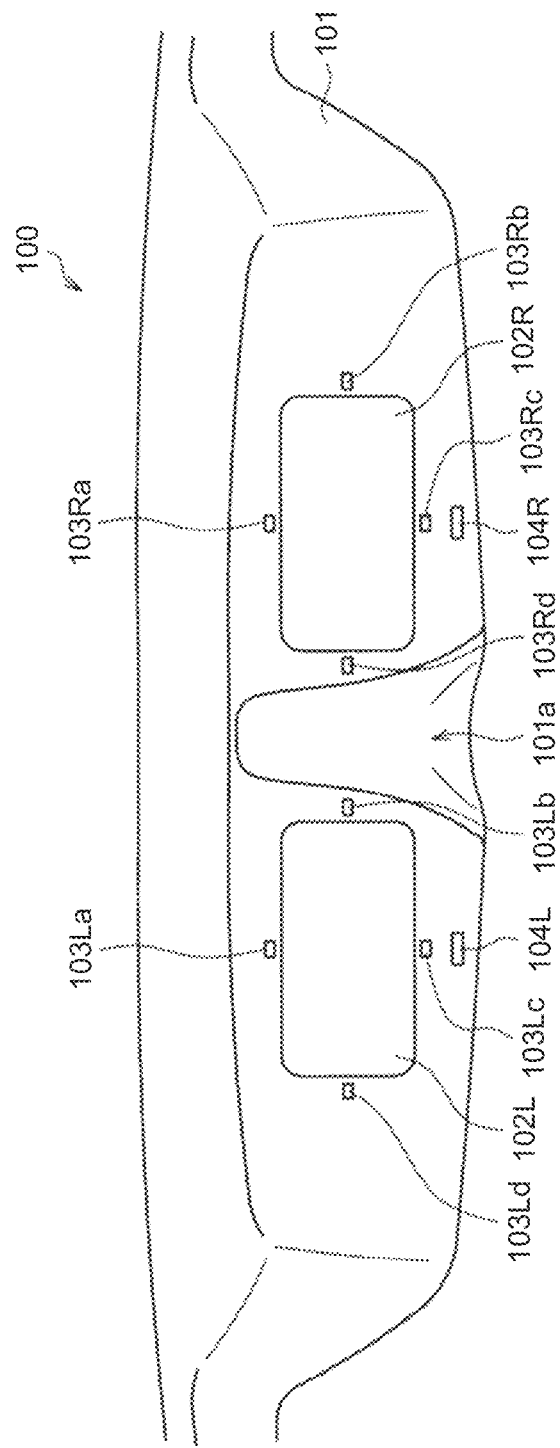
FIG. 3 is an explanatory diagram illustrating the configuration of a display device according to the embodiment on a side facing the eyes of a user.
Figure 4:
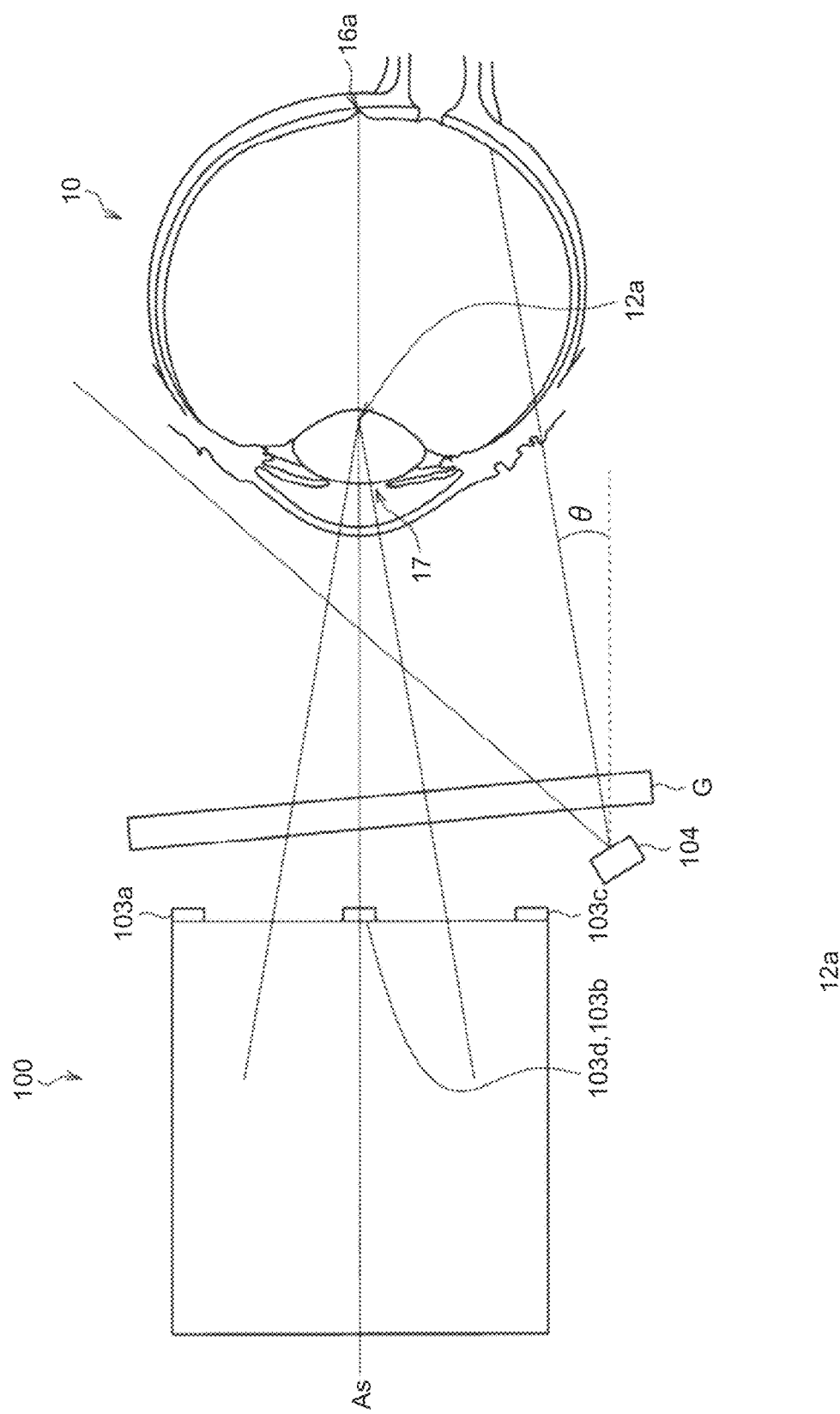
FIG. 4 is a schematic side view illustrating the positional relation between an eyeball 10 of the user and the display device when the display device according to the embodiment is mounted.

Before describing the information processing device according to the present embodiment, the following describes a hardware configuration of a display device 100 on which calibration is performed by the information processing device according to the present embodiment with reference to FIGS. 3 and 4. FIG. 3 is an explanatory diagram illustrating the configuration of the display device 100 on a side facing the eyes of the user. FIG. 4 is a schematic side view illustrating the positional relation between the eyeball 10 of the user and the display device 100 when the display device 100 is mounted.

The display device 100 is mounted on the head of the user and used while a display unit is positioned opposite to each eye. The display device 100 may be a head-mounted display of a non-transmissive type, a video transmissive type, an optical transmissive type, or the like. As illustrated in FIG. 3, display units 102R and 102L are provided at positions corresponding to the right eye and the left eye, respectively, on a surface of the display device 100 according to the present embodiment on the side facing the eyes of the user. The display units 102R and 102L according to the present embodiment are each formed in a substantially rectangular shape. A housing 101 may include a recess 101a in which the nose of the user is positioned between the display units 102R and 102L.

Four light sources 103Ra, 103Rb, 103Rc, and 103Rd are provided around the display unit 102R substantially at the respective centers of four sides of the display unit 102R. Similarly, four light sources 103La, 103Lb, 103Lc, and 103Ld are provided around the display unit 102L substantially at the respective centers of four sides of the display unit 102L. The light sources 103Ra to 103Rd and 103La to 103Ld are made of light sources configured to emit infrared light. The light sources 103Ra to 103Rd and 103La to 103Ld emit light to the eyeballs 10 of the user facing the display units 102R and 102L provided with the light sources.

Image capturing units 104R and 104L configured to capture images of the eyeballs 10 are provided around the display units 102R and 102L, respectively. For example, the image capturing units 104R and 104L are provided below the display units 102R and 102L (below the light sources 103Rc and 103Lc provided below the respective display units 102R and 102L) as illustrated in FIG. 3. As illustrated in FIG. 4, the image capturing units 104R and 104L are each disposed so that at least the pupil 17 of the eyeball 10 to be captured is included in the image capturing range thereof. For example, the image capturing units 104R and 104L are each disposed to have a predetermined elevation θ. The elevation θ may be, for example, 30° approximately.

The display device 100 is configured so that the display units 102R and 102L are each separated from the eyeball 10 of the user by a predetermined distance when the display device 100 is mounted on the user. Accordingly, the user on which the display device 100 is mounted can have, in the visual field, the display regions of the display units 102R and 102L without uncomfortable feeling. In this case, when eye glasses G are mounted on the user, the distance between each of the display units 102R and 102L and the corresponding eyeball 10 of the user may be determined so that the display device 100 can be mounted over the eye glasses G. The image capturing units 104R and 104L are each disposed so that the pupil 17 of the eyeball 10 of the user is included in the image capturing range thereof in this state.

<<1.3. Functional Configuration>>

Figure 5:
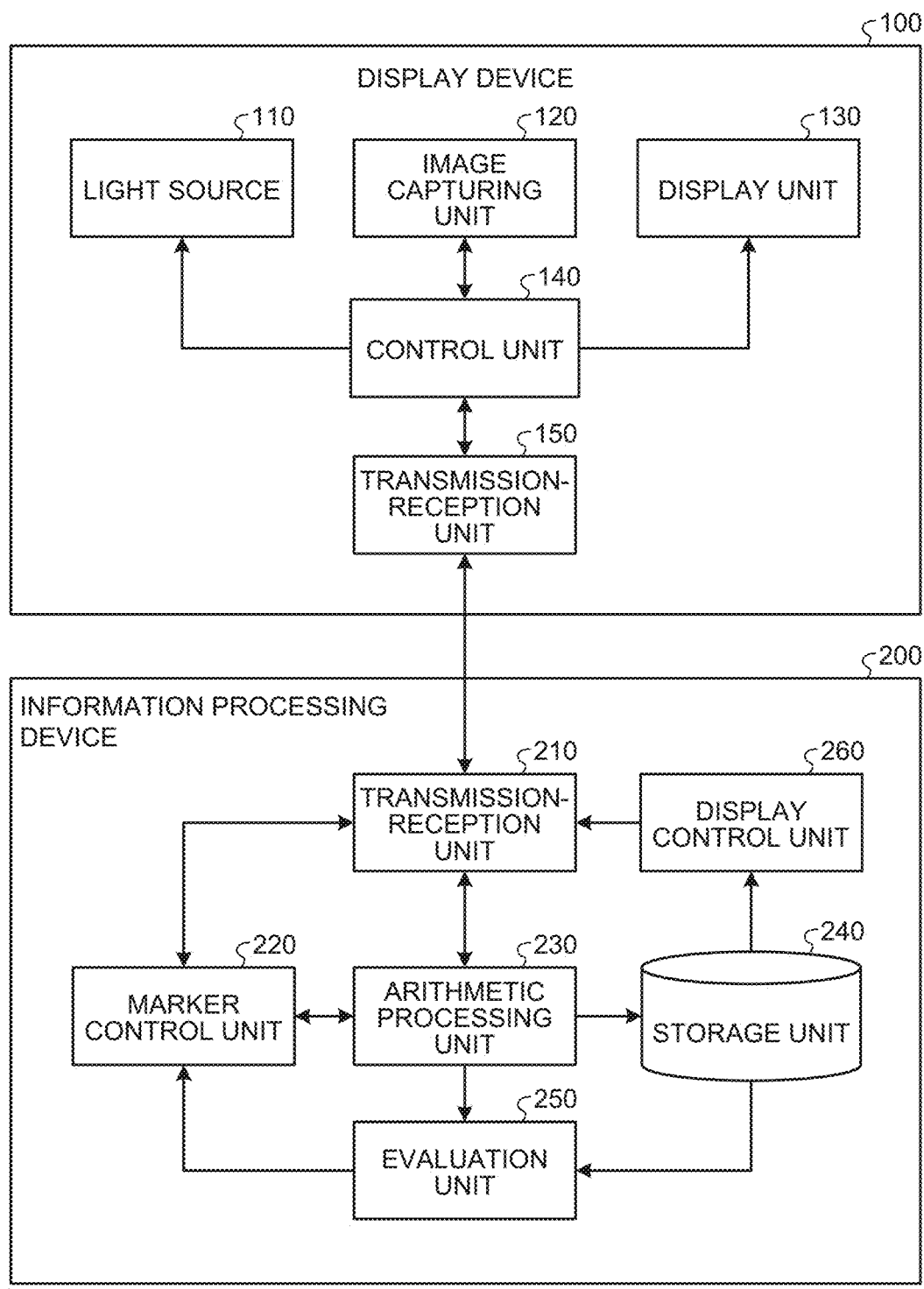
FIG. 5 is a functional block diagram illustrating functional configurations of the display device and an information processing device according to the embodiment.

The following describes functional configurations of the above-described display device 100 and an information processing device 200 configured to perform calibration of the display device 100 based on FIG. 5. FIG. 5 is a functional block diagram illustrating the functional configurations of the display device 100 and the information processing device 200.

(Display Device 100)

As illustrated in FIG. 5, the display device 100 includes a light source 110, an image capturing unit 120, a display unit 130, a control unit 140, and a transmission-reception unit 150.

The light source 110 emits light to each eyeball 10 of the user on which the display device 100 is mounted. The light source 110 is, for example, a light source configured to emit infrared light, and corresponds to the light sources 103Ra to 103Rd and 103La to 103Ld in FIG. 3. The light source 110 emits the light based on an instruction from the control unit 140.

The image capturing unit 120 captures an image of each eyeball 10 of the user on which the display device 100 is mounted. The image capturing unit 120 corresponds to the image capturing units 104R and 104L in FIG. 3. The image capturing unit 120 performs the image capturing based on an instruction from the control unit 140, and outputs the captured image to the control unit 140.

The display unit 130 is an output unit configured to display information. The display unit 130 corresponds to the display units 102R and 102L in FIG. 3. The display unit 130 may be, for example, a liquid crystal display, an organic EL display, or a lens on which information is displayed by a projection device. The display unit 130 performs various kinds of information display based on control of a display control unit 260 of the information processing device 200 to be described later.

The control unit 140 controls the entire function of the display device 100. For example, the control unit 140 controls lighting of the light source 110 and controls image capturing of the image capturing unit 120. In addition, the control unit 140 controls information transmission to and reception from the information processing device 200 through the transmission-reception unit 150.

The transmission-reception unit 150 is an interface through which information is transmitted to and received from an external instrument. In the present embodiment, the display device 100 performs calibration through transmission and reception of information to and from the information processing device 200. In this case, an image captured by the image capturing unit 120 is transmitted from the display device 100 to the information processing device 200 through the transmission-reception unit 150. In addition, for example, information of lighting control of the light source 110 in calibration, image capturing control information that causes the image capturing unit 120 to perform image capturing, and display information to be displayed on the display unit 130, which are transmitted from the information processing device 200 are received through the transmission-reception unit 150.

(Information Processing Device 200)

As illustrated in FIG. 5, the information processing device 200 includes a transmission-reception unit 210, a marker control unit 220, an arithmetic processing unit 230, a storage unit 240, an evaluation unit 250, and the display control unit 260.

The transmission-reception unit 210 is an interface through which information is transmitted to and received from an external instrument. In the present embodiment, the transmission-reception unit 210 transmits and receives information for executing calibration to and from the display device 100. In this case, the transmission-reception unit 210 transmits, to the display device 100, for example, information of lighting control of the light source 110 in calibration, image capturing control information that causes the image capturing unit 120 to perform image capturing, and display information to be displayed on the display unit 130. In addition, the transmission-reception unit 210 transmits a display control signal generated by the display control unit 260 to the display device 100. In addition, the transmission-reception unit 210 receives an image captured by the image capturing unit 120 and the like from the display device 100.

The marker control unit 220 performs display control of a gaze point marker displayed on the display unit 130 of the display device 100 in calibration. The gaze point marker is an object displayed in each display region to measure the offset between the optical axis and the visual axis of the user. When the sight line of the user points to the displayed gaze point marker, a vector (hereinafter also referred to as "marker vector") from the pupil center of the user to the gaze point marker can be obtained, and the optical axis of the user in this case can be estimated.

The marker control unit 220 sequentially displays the gaze point marker at each predetermined position (hereinafter also referred to as "calibration point") so that sight line data of the user is acquired at a plurality of positions in the display region. The marker control unit 220 acquires the sight line data of the user at all calibration points by repeating processing in which, once a predetermined number of pieces of sight line data are acquired at a calibration point at which the gaze point marker is displayed, the gaze point marker is moved to the next calibration point.

In this case, the marker control unit 220 moves the gaze point marker between calibration points while the gaze point marker is displayed. Accordingly, the user moves the sight line to follow the gaze point marker, and thus time for searching for the gaze point marker displayed at each calibration point is unnecessary and movement of the sight line pointing to the gaze point marker can be stabilized as compared to a case in which the gaze point marker is intermittently displayed.

The marker control unit 220 may control the moving speed of the gaze point marker being moved between calibration points. When the gaze point marker is moved at a constant speed, the sight line is harder to stabilize when the gaze point marker is displayed at the destination calibration point. Thus, the marker control unit 220 may perform control to decrease the moving speed of the gaze point marker being moved between calibration points as the gaze point marker comes closer to the destination calibration point. With this configuration, the gaze point marker moves fast right after the start of movement, but the movement slows down as the gaze point marker comes closer to the destination calibration point. Since the sight line of the user moves along with the moving speed of the gaze point marker, the movement of the sight line of the user slows down as the gaze point marker comes closer to the destination calibration point, and thus the sight line is easier to be stabilized when the gaze point marker is displayed at the calibration point.

The arithmetic processing unit 230 calculates the optical axis of the user and the marker vector when the gaze point marker is displayed at each calibration point. The arithmetic processing unit 230 acquires, from the display device 100, images obtained through image capturing of the eyes of the user gazing at the gaze point marker while the eyeballs of the user are irradiated with light from the light sources, and calculates the optical axis of the user and the marker vector. The optical axis and the marker vector thus calculated are stored in the storage unit 240 for each calibration point.

It is one characteristic of the arithmetic processing unit 230 to determine calibration executability for each eye based on the sight line data and use only the sight line data of an eye for which calibration is determined to be executable when executing the calibration for the eye.

The storage unit 240 stores various kinds of information necessary in calibration of the display device 100. The storage unit 240 stores, for example, movement information that defines the position of a calibration point at which the gaze point marker is displayed and how the gaze point marker is to be moved, and setting information such as the number of pieces of sight line data to be acquired at each calibration point and a threshold used in calibration end determination. In addition, the storage unit 240 stores sight line data calculated by the arithmetic processing unit 230.

The evaluation unit 250 evaluates variance of the optical axis of the user estimated at each calibration point. The arithmetic processing unit 230 determines calibration executability by, for example, determining whether the variance is in an allowable range. Details of this determination processing will be described later.

The display control unit 260 controls the display position of an object displayed on the display unit 130 in accordance with an eye for which calibration has been executed. In this case, the display control unit 260 displays the object in an area corresponding to the eye for which calibration has been executed. Details of display control by the display control unit 260 will be described later.

The functional configurations of the display device 100 and the information processing device 200 have been described above. In FIG. 5, the information processing device 200 that performs calibration processing is illustrated separately from the display device 100, but the present disclosure is not limited to such an example. For example, some or all functions of the information processing device 200 illustrated in FIG. 5 may be achieved as functions of the display device 100.

<<1.4. Calibration Processing>>

The following describes calibration processing of the display device 100 by the information processing device 200 according to the present embodiment with reference to FIGS. 6 to 10. The calibration processing of the display device 100 by the information processing device 200 according to the present embodiment starts by displaying the gaze point marker on the display unit 130 and prompting the user to point the sight line to the gaze point marker. Display control of the gaze point marker is performed by the control unit 140 upon reception of an instruction from the marker control unit 220 of the information processing device 200. In calibration, the sight line data of the user is acquired at a plurality of positions in the display region of the display unit 130. When the gaze point marker is displayed at each calibration point as a position at which the sight line data is acquired, the user is prompted to intentionally point the sight line to the gaze point marker, which allows acquisition of the sight line data.

Figure 6:
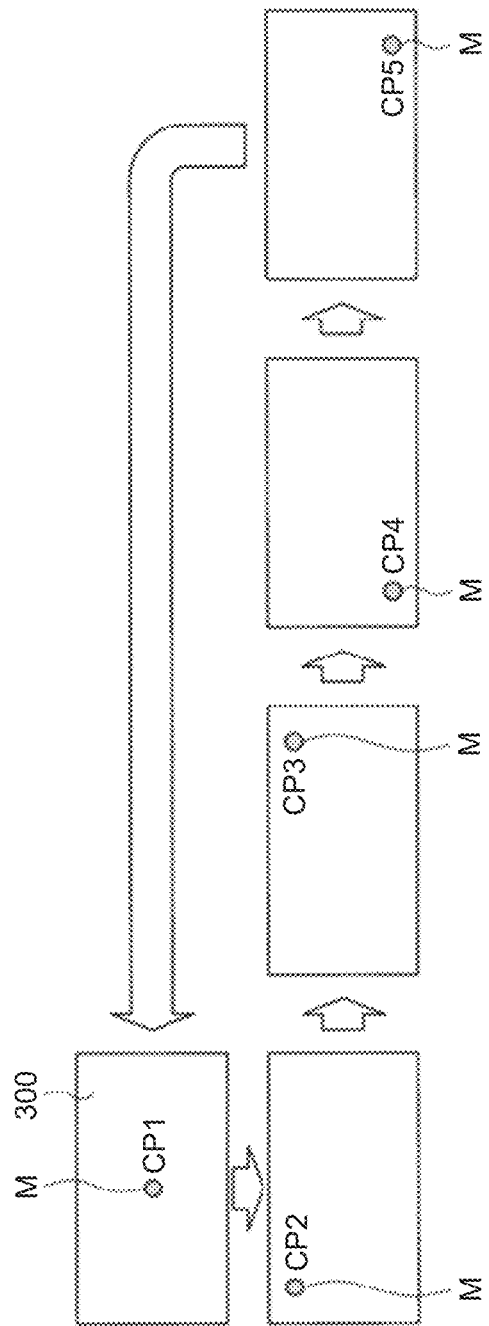
FIG. 6 is an explanatory diagram illustrating exemplary display of a gaze point marker displayed and moved according to the embodiment.

The gaze point marker is sequentially displayed at a plurality of calibration points set in a display region 300 of the display unit 130 in advance. FIG. 6 is an explanatory diagram illustrating exemplary display of the gaze point marker displayed and moved. For example, as illustrated in FIG. 6, a gaze point marker M is first displayed at a calibration point CP1 at the center of the display region 300. When the gaze point marker M is displayed at the calibration point CP1, the user points the sight line to the gaze point marker M. The sight line of the user can be fixed to the calibration point CP1 by keeping the gaze point marker M displayed, and the sight line data is acquired in this state.

After the sight line data at the calibration point CP1 is acquired, the gaze point marker M is moved to a calibration point CP2 at an upper-left part of the display region 300 as the next acquisition position of the sight line data while being kept displayed. Then, the sight line data at the calibration point CP2 is acquired. Thereafter, the sight line data acquisition and the movement are repeated at a calibration point CP3 at an upper-right part of the display region 300, a calibration point CP4 at a lower-left part of the display region 300, and a calibration point CP5 at a lower-right part of the display region 300.

When the gaze point marker M is displayed at the first calibration point, the sight line data of the user at the calibration point is acquired. The sight line data includes an optical axis vector indicating the direction of an estimated sight line of the user, and the marker vector from the pupil center of the user to the gaze point marker. The sight line data is acquired for each of the left eye and the right eye.

(Calculation of Optical Axis Vector)

Figure 7:
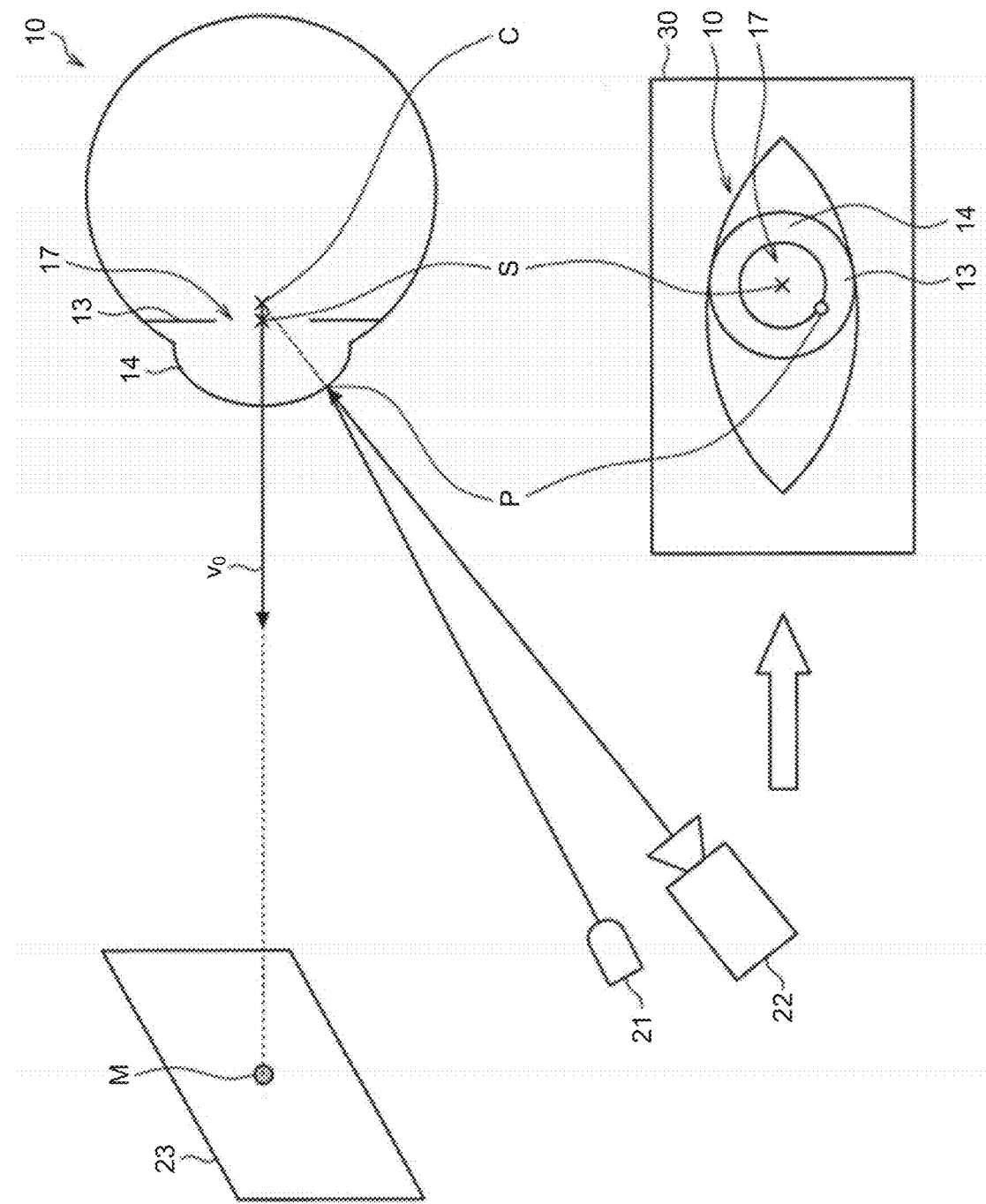
FIG. 7 is an explanatory diagram for describing optical axis vector calculation processing using a pupil cornea reflection method according to the embodiment.

The arithmetic processing unit 230 estimates the optical axis vector by, for example, the pupil cornea reflection method. The following describes optical axis estimation processing by the pupil cornea reflection method with reference to FIG. 7. FIG. 7 is an explanatory diagram for describing optical axis vector calculation processing by the pupil cornea reflection method. In the pupil cornea reflection method, the eyeball 10 of the user observing a display surface 23 of the display unit is irradiated with light from a light source 21, and an image of the eyeball 10 being irradiated with the light is captured by an image capturing unit 22. Then, the optical axis is estimated based on a captured image 30 obtained by the image capturing unit 22. For simplification of description, the following description is made on a case in which the eyeball 10 is irradiated by one light source 21.

As illustrated in FIG. 7, the user gazes at the gaze point marker M displayed on the display surface 23. In this case, the eyeball 10 is irradiated with light by the light source 21, and an image of the eyeball 10 is captured by the image capturing unit 22. As illustrated in FIG. 7, the cornea 14, an iris 13, and the pupil 17 of the eyeball 10 of the user are captured in the captured image 30 of the eyeball 10 thus acquired. In addition, a Purkinje image P as a bright spot of irradiation light emitted from the light source 21 to the eyeball 10 is captured in the captured image 30.

After the captured image 30 is acquired, optical axis calculation processing is performed. The optical axis calculation processing is performed by the arithmetic processing unit 230. Thus, first, a pupil center S and the Purkinje image P are detected from the captured image 30. This detection processing may be performed by a well-known image recognition technology.

For example, various kinds of image processing (for example, adjustment processing of distortion, black level, and white balance) on the captured image 30, and the processing of acquiring luminance distribution in the captured image 30 are performed in the processing of detecting an image of the pupil 17. In addition, for example, the processing of detecting the outline (edge) of the image of the pupil 17 based on the acquired luminance distribution, and the processing of approximating the detected outline of the image of the pupil 17 with a figure such as a circle or an ellipse may be performed. The pupil center S can be calculated from the detected image of the pupil 17.

In the processing of detecting the Purkinje image P, a series of processing such as various kinds of image processing on the captured image 30, the processing of acquiring the luminance distribution in the captured image 30, and the processing of detecting a pixel having a relatively large luminance value difference from surrounding pixels based on the luminance distribution may be performed. The center of the Purkinje image P may be detected from the detected Purkinje image P.

Then, the three-dimensional coordinates of the pupil center S and a curvature center point C of the cornea 14 are calculated. The curvature center point C of the cornea 14 is the center of a sphere when the cornea 14 is regarded as part of the sphere. The three-dimensional coordinate of the pupil center S is calculated based on the image of the pupil 17 detected from the captured image 30. Specifically, the three-dimensional coordinate of each point on the outline of the image of the pupil 17 in the captured image 30 is calculated based on, for example, the positional relation between the image capturing unit 22 and the eyeball 10, light refraction at the surface of the cornea 14, and the distance between the curvature center point C of the cornea 14 and the pupil center S. The central point of these coordinates is set as the three-dimensional coordinate of the pupil center S.

The curvature center point C of the cornea 14 is calculated based on the Purkinje image P detected from the captured image 30 and the center of the Purkinje image P. Specifically, a position separated from the surface of the cornea 14 by the curvature radius of the cornea 14 toward the inside of the eyeball 10 on a straight line connecting the image capturing unit 22 and the center of the Purkinje image P is calculated as the three-dimensional coordinate of the curvature center point C of the cornea 14 based on the positional relation among the light source 21, the image capturing unit 22, and the eyeball 10, and the curvature radius of the cornea 14.

A straight line connecting the curvature center point C of the cornea 14 and the pupil center S calculated in this manner is an estimated optical axis. In other words, the coordinate of a position at which the optical axis intersects the display surface 23 is an estimated position of the sight line of the user. An optical axis vector vo is set to be a vector from the curvature center point C of the cornea 14 toward the pupil center S.

(Calculation of Marker Vector)

The marker vector from the pupil center S of the user to the gaze point marker M can be calculated as a vector from the pupil center S specified from the captured image 30 as described above toward a position on the display surface 23 at which the gaze point marker M is currently displayed.

In this manner, the arithmetic processing unit 230 acquires, as the sight line data, the optical axis vector and the marker vector for each of the left eye and the right eye through calculation. The sight line data for each of the left eye and the right eye, which is acquired by the arithmetic processing unit 230 is stored in the storage unit 240.

(Reduction of Detection Result Variance)

The arithmetic processing unit 230 determines whether the calculated optical axis vector vo is information usable as a calibration detection result.

Specifically, the arithmetic processing unit 230 may determine whether deviation of the optical axis vector vo is within a predetermined range to check that the calculated optical axis vector vo does not largely deviate from any optical axis vector vo acquired so far. The optical axis vector vo calculated by the arithmetic processing unit 230 is stored in the storage unit 240 as a history. By using this history, the arithmetic processing unit 230 checks, for example, whether the angle between an optical axis vector average vo_ave acquired through past N calculations including the current calculation and the current optical axis vector vo is equal to or smaller than a predetermined value. When the angle between the optical axis vector average vo_ave and the current optical axis vector vo exceeds such a predetermined threshold, the currently calculated optical axis vector vo is determined to have large deviation, and is not used a calibration detection result. Accordingly, the accuracy of the optical axis vector can be improved.

The optical axis vector average vo_ave may be calculated by using, for example, past three optical axis vectors vo. The threshold for determining the angle between the optical axis vector average vo_ave and the current optical axis vector vo may be, for example, 3° approximately. When the optical axis vector vo is calculated from an image captured while the user is not gazing at the gaze point marker M, the calculated optical axis vector vo largely deviates from the optical axis vector average vo_ave. Such an optical axis vector vo can be excluded as a detection result through the determination.

The arithmetic processing unit 230 may determine, for example, whether an angle $\omega$ between a calculated marker vector vm and the optical axis vector vo is equal to or smaller than a predetermined value. Through such determination, it can be checked whether the estimated optical axis vector vo largely deviates from the actual direction of the sight line. The threshold value thus used is determined while taking into account the difference between the optical axis and the visual axis, error in the optical axis detection, and the like.

For example, the estimated direction of the sight line of the user (in other words, the optical axis) is not necessarily aligned with the direction (in other words, the visual axis) in which the user is actually gazing. This is attributable to the shape and size of each eyeball, disposition of the retina and the optic nerve in the eyeball, and the like. The optical axis and the visual axis are normally offset from each other by 4° to 8°, depending on the individual. It is thought that the error in the optical axis detection is several degrees, for example, ±3°. This error is combined with other accumulation error of ±1°, thereby expecting generation of error of 0° to 12° approximately. In this case, when the angle $\omega$ between the calculated marker vector and the optical axis vector is 0° to 12°, the calculated optical axis vector vo may be determined to have an acceptable accuracy, and may be used as a calibration detection result.

When such determination processing is performed, variance of detection results can be reduced to improve the accuracy of the optical axis vector.

(False Detection Determination)

When the above-described determination for reducing detection result variance is successful, false places are still detected as the pupil and the bright spot in some cases. The calibration processing cannot be correctly performed by using false detection results. Thus, the arithmetic processing unit 230 may perform false detection determination processing for not using such a false detection result as a calibration detection result. For example, when calculated sizes of the right and left pupils are extremely different from each other, it is highly likely that a false place is recognized as a pupil. The sight line data acquired in such a case is not used a detection result. Specifically, for example, when the size ratio of the right and left pupils exceeds a predetermined value (for example, 1.2), it may be determined that the sizes of the right and left pupils are extremely different from each other, and the acquired sight line data is not used as a detection result.

After the above-described processing is performed, the arithmetic processing unit 230 determines whether at least a predetermined number of pieces of usable sight line data have been acquired at a calibration point at which current the gaze point marker M is displayed. When at least the predetermined number of pieces of usable sight line data have been acquired in a predetermined time, the arithmetic processing unit 230 stores the calibration point in the storage unit 240 as a usable calibration point. The arithmetic processing unit 230 executes the above-described determination processing for each of the left eye and the right eye.

Subsequently, the arithmetic processing unit 230 determines whether the sight line data has been acquired at all calibration points. When there is a calibration point at which the sight line data is yet to be acquired, the arithmetic processing unit 230 instructs the marker control unit 220 to move the gaze point marker M to the next calibration point. The marker control unit 220 outputs, to the display device 100 through the transmission-reception unit 210, an instruction to move the gaze point marker M to the next calibration point set in advance.

(Gaze Point Marker Moving Processing)

The gaze point marker M is displayed to prompt the user to point the sight line thereto. Display control of the gaze point marker M is performed to correctly acquire the sight line data of the user in a short time.

First, the gaze point marker M is moved between calibration points while being displayed. Accordingly, the user moves the sight line to follow the gaze point marker, and thus time for searching for the gaze point marker M displayed at each calibration point is unnecessary and movement of the sight line pointing to the gaze point marker can be stabilized as compared to a case in which the gaze point marker M is intermittently displayed.

Then, the moving speed of the gaze point marker M being moved between calibration points is changed. When the gaze point marker M is moved at a constant speed, the sight line is harder to stabilize when the gaze point marker M is displayed at the destination calibration point. Thus, the marker control unit 220 performs control to decrease the moving speed of the gaze point marker M being moved between calibration points as the gaze point marker M comes closer to the destination calibration point. With this configuration, the gaze point marker M moves fast right after the start of movement, but the movement slows down as the gaze point marker M comes closer to the destination calibration point. Since the sight line of the user moves along with the moving speed of the gaze point marker, the movement of the sight line of the user slows down as the gaze point marker M comes closer to the destination calibration point, and thus the sight line is harder to be stabilized when the gaze point marker M is displayed at the calibration point.

Calibration points at which the sight line data is acquired in the display region 300 are typically set to be near the center of the display region 300 as a position that the user views when facing front, and peripheral parts of the display region 300 where the difference between the visual axis and the optical axis is likely to be large. Typically, a plurality of calibration points (for example, five to nine points) are set in the visual field. When calibration is performed at these positions, correction processing can be performed so that appearance is uniform in the entire display region 300. Specifically, calibration may be performed at the center and four corners of the rectangular display region 300. Alternatively, calibration may be performed at the center of the rectangular display region 300 and near the center of each side thereof.

When the gaze point marker M is moved to each calibration point, the order of movement of the gaze point marker M may be determined to increase the travel distance as much as possible. Since the user moves the sight line along with movement of the gaze point marker M, it is difficult to point the sight line to the gaze point marker M displayed at the next calibration point when the travel distance of the gaze point marker M is short, and as a result, the difference between the visual axis and the optical axis increases. In addition, the difference between the visual axis and the optical axis is likely to increase when the gaze point marker M is moved in the horizontal direction of the display region 300, and thus the gaze point marker M may be moved to have movement in upward and downward directions such as the vertical direction and oblique directions.

For example, when the sight line data is acquired at five calibration points CP1 to CP5 set at the center and four corners of the display region 300, the gaze point marker M may be moved in a zig-zag manner through the calibration points CP2 to CP5 at the four corners after the calibration point CP1 at the center is displayed. When the sight line data is acquired at five calibration points CP1 to CP5 set at the center and near the center of each side, for example, the calibration points CP1 to CP4 near the centers of the respective sides are first sequentially displayed to draw a rhombus locus. Thereafter, the calibration point CP1 at the center may be displayed.

After the gaze point marker M is moved to the next calibration point, the sight line data acquisition is performed at the destination calibration point. Thereafter, the processing is repeatedly executed until the sight line data acquisition is completed at all calibration points.

(Calibration Executability Determination)

After the sight line data is acquired at all calibration points, the arithmetic processing unit 230 determines calibration executability for each of the left eye and the right eye. In this case, the arithmetic processing unit 230 may determine calibration executability for the left eye and the right eye based on any usable calibration point. More specifically, when the number of usable calibration points is smaller than a threshold, the arithmetic processing unit 230 may determine that calibration is inexecutable for the corresponding eye. The arithmetic processing unit 230 may determine that calibration is inexecutable for the corresponding eye when the number of usable calibration points is smaller than three.

When the number of usable calibration points is equal to or larger than the threshold, variance of the optical axis vector vo is evaluated by the evaluation unit 250. The arithmetic processing unit 230 may determine the calibration executability for each eye based on the variance of the optical axis vector evaluated by the evaluation unit 250.

Figure 9:
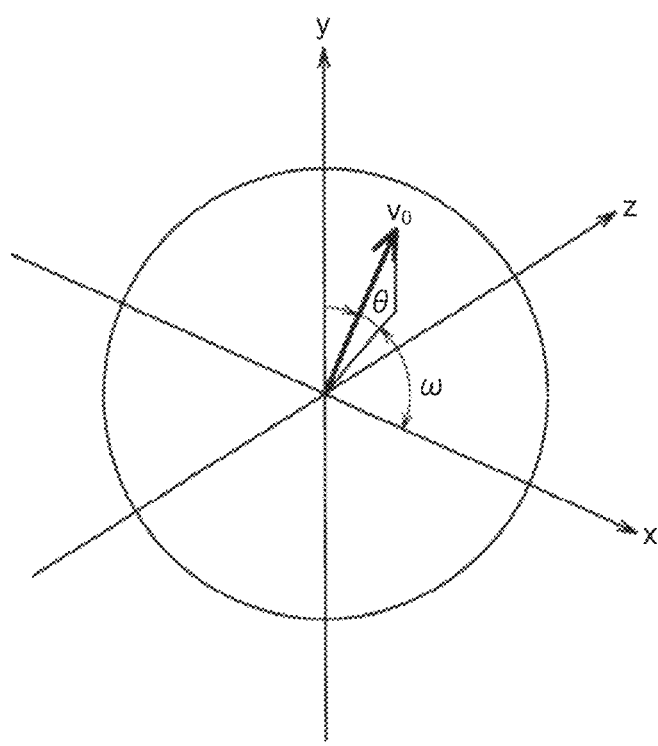
FIG. 9 is an explanatory diagram illustrating the coordinates of a marker vector and an optical axis vector according to the embodiment.

When correctly estimated, the optical axis vector vo at each calibration point has a value corresponding to the display position of the calibration point in the display region 300. FIG. 8 illustrates an exemplary result of detection of the optical axis vector vo when calibration is performed at the calibration points CP1 to CP5 illustrated in FIG. 6. FIG. 8 is a graph illustrating an exemplary result of evaluation of optical axis variance. FIG. 8 indicates the relation between an angle θ of the optical axis vector vo in the vertical direction and an angle ω of the optical axis vector vo in the horizontal direction. In the present embodiment, the optical axis vector vo is defined based on coordinate axes illustrated in FIG. 9. FIG. 9 is an explanatory diagram illustrating the coordinates of the marker vector and the optical axis vector. Among the coordinate axes in FIG. 9, the x axis represents the horizontal direction of the display region 300, the y axis represents the vertical direction of the display region 300, and the z axis represents the depth direction of the display region 300. The angle θ is the angle between the optical axis vector vo and the zx plane, and the angle ω is the angle between the optical axis vector vo and the xy plane.

The upper part of FIG. 8 illustrates distribution of the optical axis vector vo when calibration is correctly performed, and the lower part of FIG. 8 illustrates distribution of the optical axis vector vo when calibration is not correctly performed. As illustrated in the upper part of FIG. 8, when calibration is correctly performed, the distribution of the optical axis vector vo is clearly separated in accordance with the positions of the calibration points set at the center and four corners of the display region 300.

As illustrated in the lower part of FIG. 8, when calibration is not correctly performed, for example, the angle θ of the optical axis vector vo in the vertical direction is substantially identical between the calibration points at the upper-right part, the upper-left part, and the center of the display region 300, and thus clear distribution is not achieved. Such distribution is particularly likely to occur for a user wearing hard contact lenses, and a user having half-closed or squinted eyes.

Thus, in the present embodiment, the evaluation unit 250 calculates a coefficient of correlation between the marker vector vm and the optical axis vector vo as an evaluation value for evaluating variance of the optical axis vector vo as a whole. This coefficient $r_{xy}$ of correlation between the marker vector vm and the optical axis vector vo can be obtained by, for example, Mathematical (1) below.

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \quad (1)$$

In Mathematical (1), i is a number provided to each calibration point and takes a value of 1 to n. When five calibration points are set, n is 5. In addition, $x_i$ and $y_i$ represent the x and y coordinates of the optical axis vector vo, and x⁻ and y⁻ represent the x and y coordinates of the marker vector vm. Note that x⁻ and y⁻ mean that ⁻ is provided at top of x and y.

Mathematical (1) evaluates the difference between the angle θ and the angle ω of the marker vector vm and the optical axis vector vo in the vertical direction and the horizontal direction at all calibration points. The correlation coefficient $r_{xy}$ calculated by Mathematical (1) decreases as the difference between these angles increases due to misalignment of the marker vector vm and the optical axis vector vo at one or a plurality of the calibration points.

In this case, the arithmetic processing unit 230 can determine that calibration is inexecutable for the corresponding eye when the correlation coefficient $r_{xy}$ is smaller than a threshold.

As described above, the arithmetic processing unit 230 according to the present embodiment can determine calibration executability for each of the left eye and the right eye based on the number of usable calibration points and variance of the optical axis vector. In addition, the arithmetic processing unit 230 can use only the sight line data of an eye for which calibration is determined to be executable when executing calibration for the eye. According to the above-described functions of the arithmetic processing unit 230 according to the present embodiment, the sight line detection can be achieved at high accuracy by removing influence of an eye that could cause accuracy decrease.

<<1.5. Calibration Processing Process>>

Figure 10:
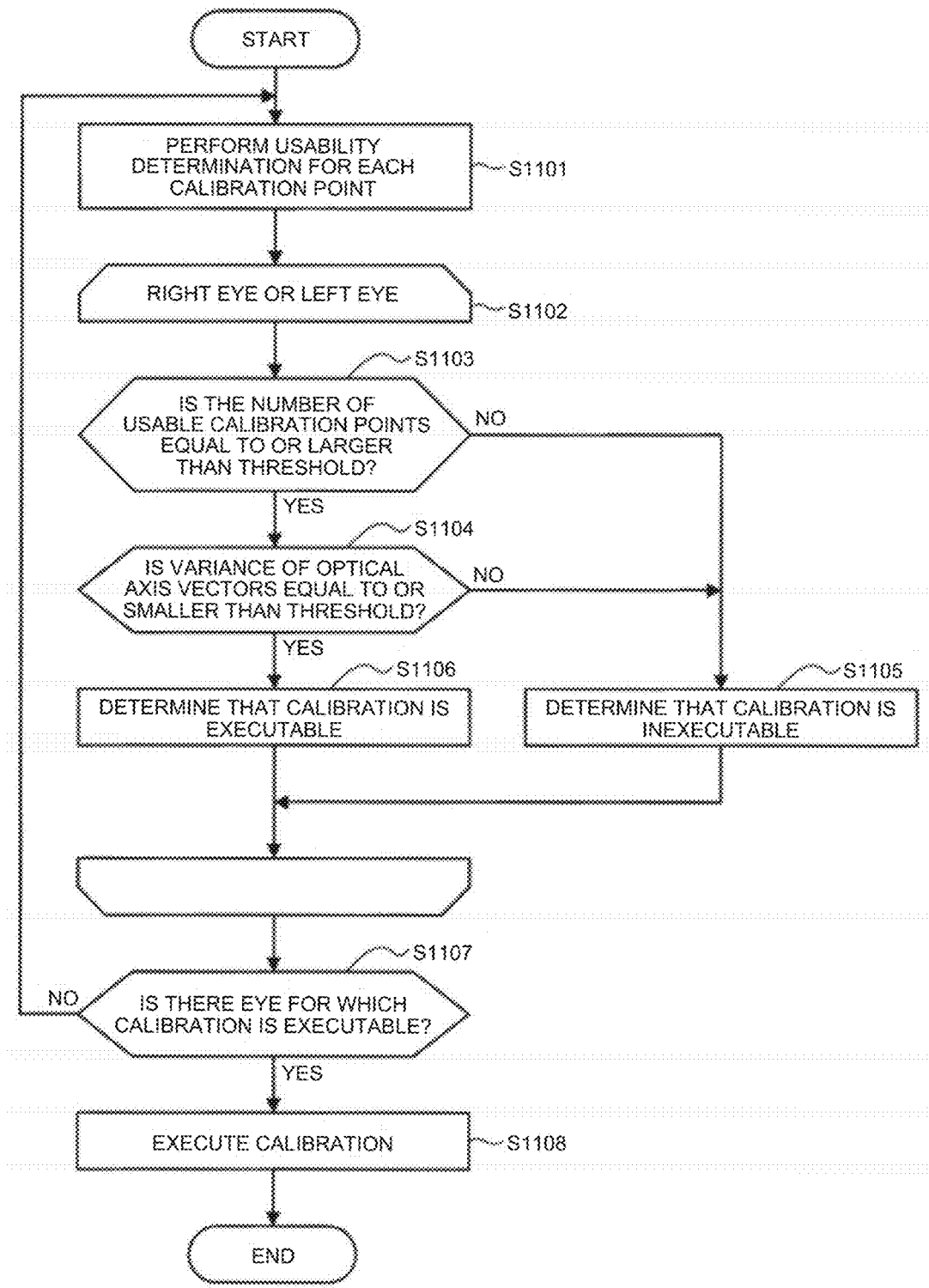
FIG. 10 is a flowchart illustrating the process of calibration processing performed by the information processing device according to the embodiment.

The following description will be made mainly on details of the process of calibration processing performed by the information processing device 200 according to the present embodiment. FIG. 10 is a flowchart illustrating the process of calibration processing performed by the information processing device 200 according to the present embodiment.

As illustrated in FIG. 10, first, the information processing device 200 performs usability determination for each calibration point (S1101). The process of the usability determination for each calibration point at step S1101 will be separately described in detail later.

Subsequently, the information processing device 200 determines calibration executability for each of the left eye and the right eye (S1102).

In the calibration executability determination, the information processing device 200 first determines whether the number of usable calibration points is equal to or larger than a threshold (S1103).

When the number of usable calibration points is smaller than the threshold (NO at S1103), the information processing device 200 determines that calibration is inexecutable for the corresponding eye (S1105).

When the number of usable calibration points is equal to or larger than the threshold (YES at S1103), the information processing device 200 subsequently determines whether variance of estimated optical axis vectors is equal to or smaller than a threshold (S1104). More specifically, the information processing device 200 can perform the above-described determination based on the correlation coefficient $r_{xy}$ of the marker vector vm and the optical axis vector vo.

When the variance of estimated optical axis vectors exceeds the threshold (NO at S1104), the information processing device 200 determines that calibration is inexecutable for the corresponding eye (S1105).

When the variance of estimated optical axis vectors is equal to or smaller than the threshold (YES at S1104), the information processing device 200 determines that calibration is executable for the corresponding eye (S1106).

After the calibration executability determination is completed for each of the left eye and the right eye, the information processing device 200 subsequently determines whether calibration is executable for at least one eye (S1107).

When calibration is executable for at least one eye (YES at S1107), the information processing device 200 executes calibration processing for each eye for which calibration is executable (S1108).

When calibration is executable for no eye (NO at S1107), the information processing device 200 may return to step S1101 to repeatedly execute the usability determination for each calibration point.

Figure 11:
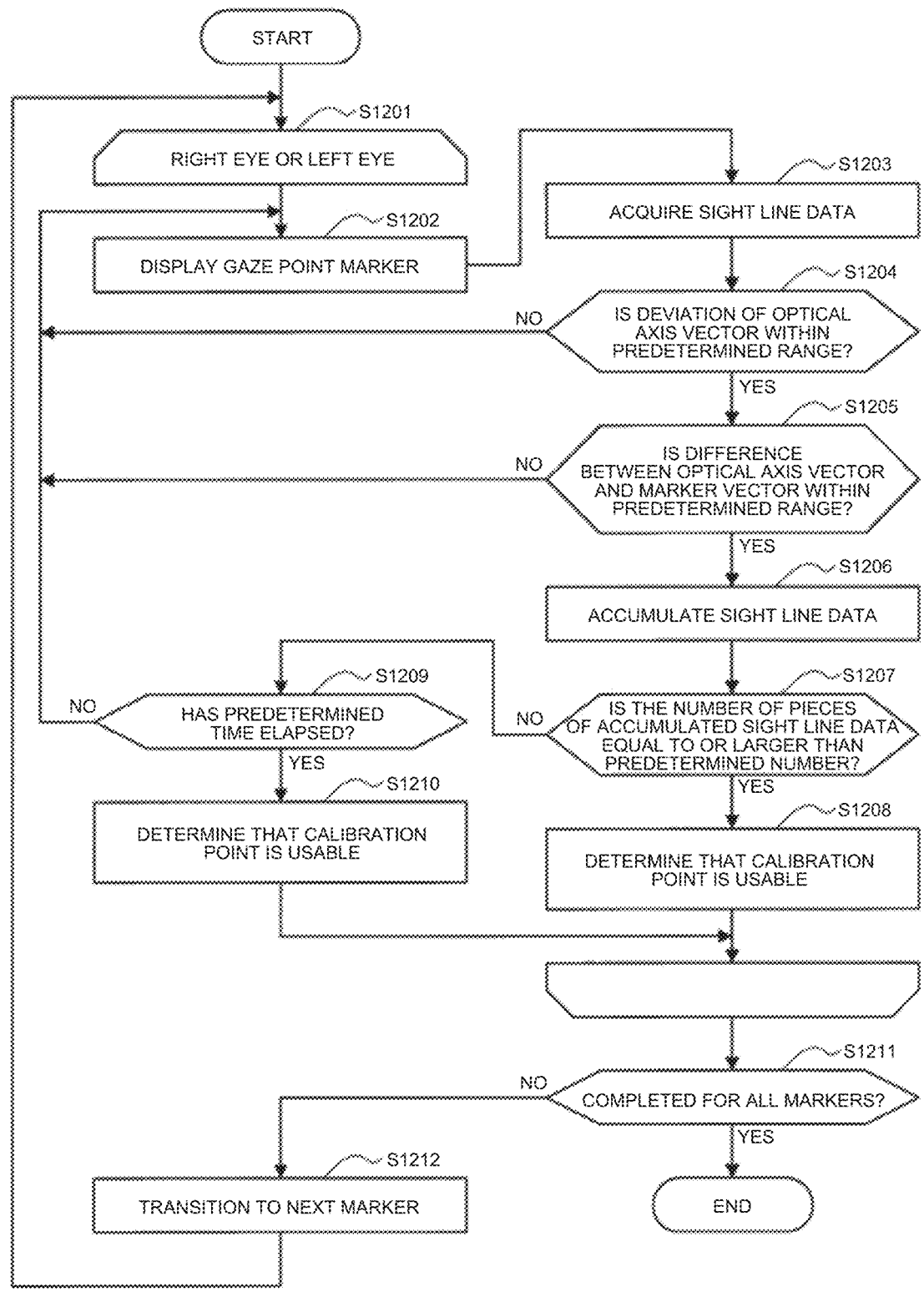
FIG. 11 is a flowchart illustrating the process of usability determination for each calibration point according to the embodiment.

Subsequently, the process of the usability determination for each calibration point at step S1101 will be described in detail below. FIG. 11 is a flowchart illustrating the process of the usability determination for each calibration point according to the present embodiment.

As illustrated in FIG. 11, the information processing device 200 performs calibration point usability determination for each of the left eye and the right eye (S1201).

In the calibration point usability determination, the information processing device 200 first displays the gaze point marker at a calibration point (S1202).

Subsequently, the information processing device 200 acquires sight line data based on a captured image including the eye of the user and obtained by image capturing when the gaze point marker is displayed at the calibration point (S1203). As described above, the sight line data includes information of the optical axis vector and the marker vector.

Subsequently, the information processing device 200 determines whether deviation of the optical axis vector is in a predetermined range based on the sight line data acquired at step S1203 (S1204).

When the deviation of the optical axis vector is not in the predetermined range (NO at S1204), the information processing device 200 returns to step S1202.

When the deviation of the optical axis vector is in the predetermined range (YES at S1204), the information processing device 200 subsequently determines whether the difference between the optical axis vector and the marker vector is in a predetermined range (S1205).

When the difference between the optical axis vector and the marker vector is not in the predetermined range (NO at S1205), the information processing device 200 returns to step S1202.

When the difference between the optical axis vector and the marker vector is in the predetermined range (YES at S1205), the information processing device 200 accumulates the sight line data acquired at step S1203 as usable sight line data (S1206).

Subsequently, the information processing device 200 determines whether the number of pieces of the accumulated sight line data is equal to or larger than a predetermined number (S1207).

When the number of pieces of the accumulated sight line data is equal to or larger than the predetermined number (YES at S1207), the information processing device 200 determines that the corresponding calibration point is usable (S1208).

When the number of pieces of the accumulated sight line data is smaller than the predetermined number (NO at S1207), the information processing device 200 subsequently determines whether a predetermined time has elapsed (S1209)

When the predetermined time has elapsed (YES at S1209), the information processing device 200 determines that the corresponding calibration point is unusable (S1210).

When the predetermined time has not elapsed (NO at S1209), the information processing device 200 returns to step S1202. In this manner, the information processing device 200 repeatedly acquires the sight line data until the number of pieces of the accumulated sight line data becomes equal to or larger than the predetermined number or until the predetermined time elapses. The predetermined time may be dynamically changed. For example, when calibration has been executed in a region, a longer time may be set for the region because it is expected that the sight line data can be acquired in the region.

When the calibration point usability is determined at step S1208 or S1209, the information processing device 200 determines whether the usability determination is completed for all calibration points (S1211).

When the usability determination is yet to be completed for all calibration points (NO at S1211), the information processing device 200 moves the gaze point marker to the next calibration (S1212), and returns to step S1201.

When the usability determination is completed for all calibration points (YES at S1211), the information processing device 200 ends the calibration point usability determination, and transitions to the processing at step S1102 in FIG. 10.

Figure 12:
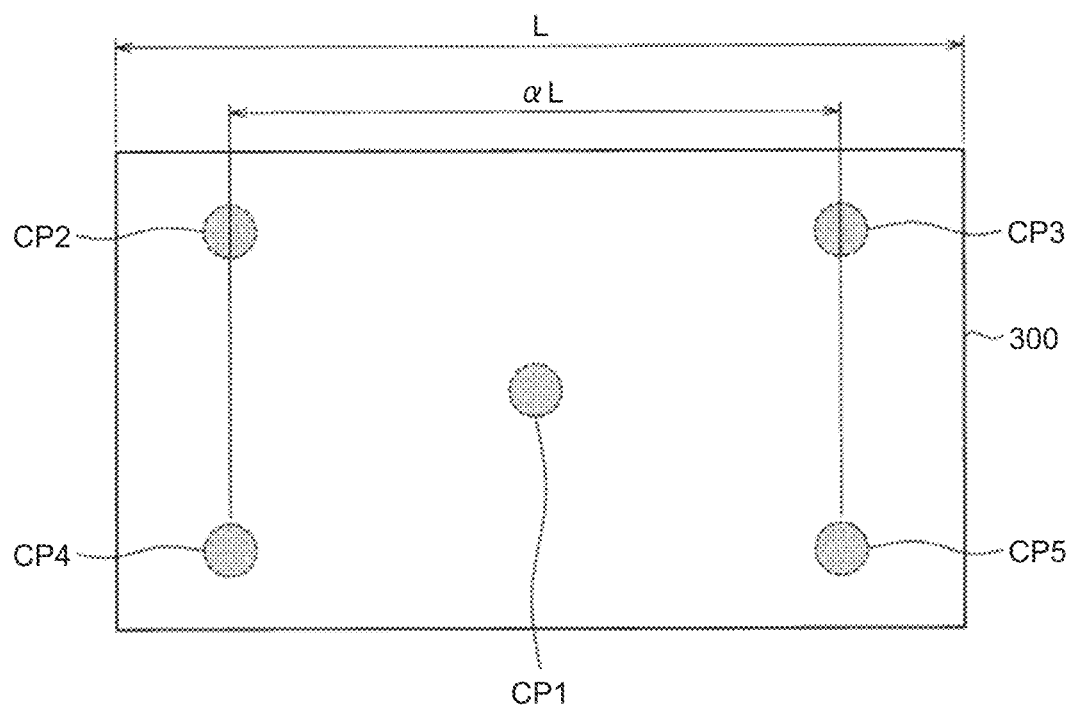
FIG. 12 is an explanatory diagram for describing change of calibration point positions according to the embodiment.

When repeatedly acquiring the sight line data as described above, the information processing device 200 may change the position of the calibration point and acquire the sight line data. FIG. 12 is an explanatory diagram for describing change of the calibration point position.

For example, as illustrated in FIG. 12, the first calibration point is set based on a region obtained by minifying the display region 300 by a predetermined ratio $\alpha$. In this case, the default values of the calibration point positions are set to be, for example, the center of the display region 300 and four corners of a region having a size equal to 90% of that of the display region. In this case, the information processing device 200 may perform change to move the calibration point positions closer to the center of the display region 300 in the above-described repetitive processing. For example, the information processing device 200 may set the calibration point positions at the four corners to four corners of a region having a size equal to 80% of that of the display region. When the calibration point positions are moved closer to the center of the display region in this manner, the user can more easily gaze at the gaze point marker, and correct sight line data is more likely to be acquired.

The process of calibration processing performed by the information processing device 200 according to the present embodiment is described in detail above. As described above, according to the information processing device 200 according to the present embodiment, even when one of the eyes does not normally function, calibration can be executed for an eye expected to be functioning normally, thereby detecting the sight line of the eye. In addition, according to the information processing device 200 according to the present embodiment, the sight line detection can be achieved at higher accuracy by removing influence of one of the eyes that could cause accuracy decrease.

In the example illustrated in FIG. 11, the information processing device 200 changes the calibration points when a predetermined number of pieces of sight line data are accumulated, but the process of the processing performed by the information processing device 200 according to the present embodiment is not limited to the example. For example, the information processing device 200 may repeat the calibration point change processing a predetermined number of times each time one piece of sight line data is accumulated.

The information processing device 200 according to the present embodiment may perform various kinds of control other than the above-described main control. For example, the information processing device 200 can improve the entire accuracy by using calibration points different from those in past calibration. The information processing device 200 may use part of a past calibration result to reduce time taken for calibration.

When it is known in advance that calibration is inexecutable for one of the eyes, for example, when the user uses an artificial eye, the information processing device 200 has no need to perform calibration executability determination for the eye.

The information processing device 200 may inform the user which of the eyes is to be used for the sight line detection in accordance with a calibration result. The information processing device 200 may present an alert or the like to the user when it is determined that calibration is inexecutable for an eye for which calibration has been performed in the past.

When the display device 100 is compatible with an augmented reality (AR) technology or the like, the information processing device 200 may perform, in accordance with surrounding brightness or the like in calibration, for example, control so that the background is difficult to visually recognize, and control so that the gaze point marker is displayed in a color distinguishable from the background.

The information processing device 200 may perform control to turn off the light source 110 and the image capturing unit 120 for an eye not used for the sight line detection, thereby effectively reducing electric power consumption. The functions of the information processing device 200 according to the present embodiment may be flexibly changed in accordance with specifications and operations.

<<1.6. Display Control Based on Calibration Execution Result>>

The following describes display control based on a calibration execution result according to the present embodiment. The display control unit 260 of the information processing device 200 according to the present embodiment can control the display position of an object displayed on the display unit 130 of the display device 100 based on the calibration execution result.

For example, assume that visual fields corresponding to the display units 102R and 102L illustrated in FIG. 3 are different from each other. When one of the eyes is not used for the sight line detection, the accuracy of the sight line detection potentially decreases in a partial region of the display unit 102 corresponding to the eye.

Thus, the display control unit 260 according to the present embodiment displays an object in an area corresponding to an eye for which calibration has been executed in the display region 300, thereby improving the accuracy of detection of the sight line toward the object.

Figure 13:
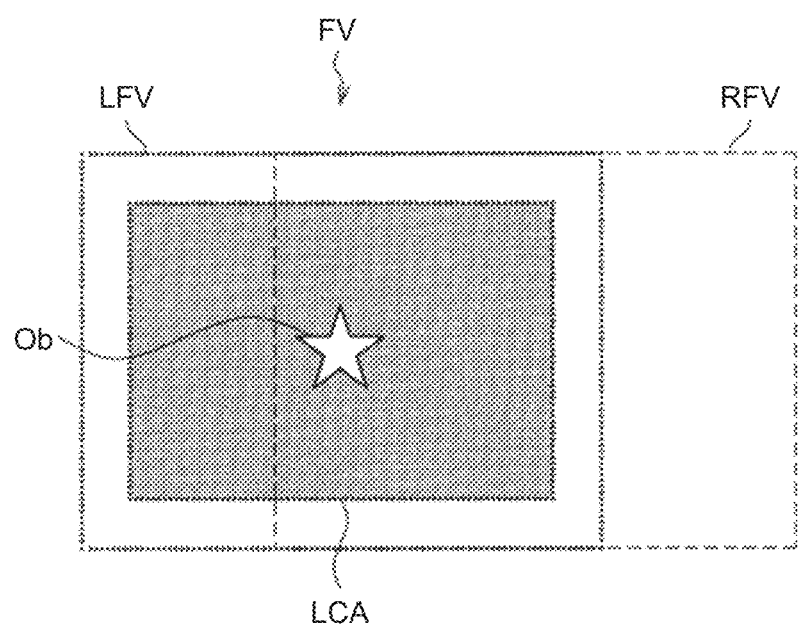
FIG. 13 is a diagram illustrating exemplary object display control performed by a display control unit according to the embodiment.

FIG. 13 is a diagram illustrating exemplary object display control performed by the display control unit 260 according to the present embodiment. FIG. 13 illustrates a visual field FV corresponding to the display unit 130. The visual field FV includes a left visual field LFV corresponding to the left eye and a right visual field RFV corresponding to the right eye.

When the arithmetic processing unit 230 does not execute calibration for the right eye but executes calibration for the left eye, the display control unit 260 may display an object Ob in an area corresponding to the left eye for which the calibration is executed.

For example, the display control unit 260 may display the object Ob closer to the left visual field LFV corresponding to the left eye in the visual field FV. In addition, the display control unit 260 may display the object Ob in a calibration area LCA of the left visual field LFV, thereby further improving the accuracy of the sight line detection for the object Ob.

The calibration area LCA is determined based on calibration points used when the calibration for the left eye is executed. For example, when the calibration points CP1 to CP5 illustrated in FIG. 12 are used in the execution of the calibration for the left eye, the calibration area LCA corresponds to a rectangular region defined by the calibration points CP2 to CP5. In this manner, the display control unit 260 according to the present embodiment can effectively improve the accuracy of the sight line detection for the object Ob by displaying the object Ob in a region used for calibration.

Figure 14:
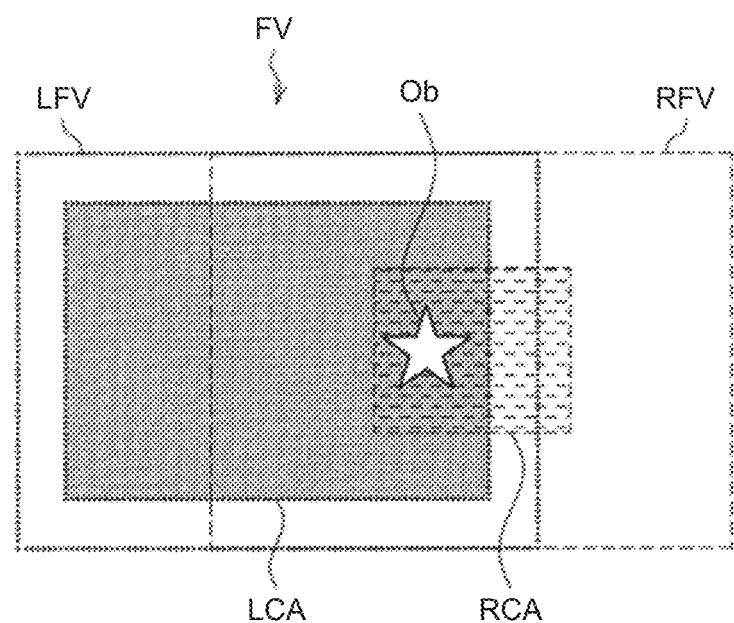
FIG. 14 is a diagram illustrating exemplary object display control according to the embodiment when calibration is executed for both the left eye and the right eye.

The display control unit 260 according to the present embodiment is not limited to the example illustrated in FIG. 13 but may perform various kinds of display control. FIG. 14 is a diagram illustrating exemplary object display control when calibration is executed for both the left eye and the right eye. FIG. 14 illustrates an example in which the size of the calibration area LCA for the left eye is different from the size of a calibration area RCA for the right eye. In this case, the display control unit 260 may display the object Ob in a region in which the calibration areas LCA and RCA overlap with each other as illustrated in FIG. 14. The display control unit 260 according to the present embodiment can appropriately and flexibly control the display position of the object Ob in accordance with a calibration execution result and characteristics of the display device 100, an application, and the like.

2. SECOND EMBODIMENT

<<2.1. Overview>>

Subsequently, the following describes a second embodiment of the present disclosure. The above description of the first embodiment is mainly made on a method in calibration of the sight line detection in which the information processing device 200 determines calibration executability for each of the eyes and executes calibration based on the determination.

To achieve the sight line detection using the pupil cornea reflection method as described above, it is necessary that the display device 100 includes an image capturing unit capable of capturing infrared light and a light source configured to emit the infrared light. In this case, it is desirable for the accuracy of the sight line detection that the light source is disposed near the center of the visual field of the user. However, in such disposition, the light source encumbers display of visual information by the display unit. In addition, in the above-described disposition, the light source is disposed inside the visual field of the user, which adversely causes significant degradation of viewing experience of the user.

Thus, unlike the case of the accuracy of the sight line detection, it is desirable for the viewing experience that the light source is disposed at a maximally unnoticeable position in the visual field of the user. However, for example, a display device compatible with an AR technology and a virtual reality (VR) technology is required to have a wide view angle, and thus physical constraints typically exist on disposition of the light source. In addition, the noticeability can be reduced through downsizing of the light source, but the downsizing of the light source has limitations and leads to cost increase.

A technological idea according to the second embodiment of the present disclosure has been developed with focus on the above-described points, and enables the sight line detection at high accuracy without encumbering the viewing experience of the user. To achieve this, the second embodiment of the present disclosure employs a transparent member including at least two light emission points each configured to irradiate an eye of the user with light guided from a light source. Characteristics of the transparent member according to the present embodiment will be described in detail below. The following description will be mainly made on any difference from the first embodiment, and detailed description of any functional configuration common to the first embodiment will be omitted. The second embodiment describes an example in which the display device 100 and the information processing device 200 are achieved as an integrated device.

<<2.2. Characteristics of Transparent Member>>

Figure 15:
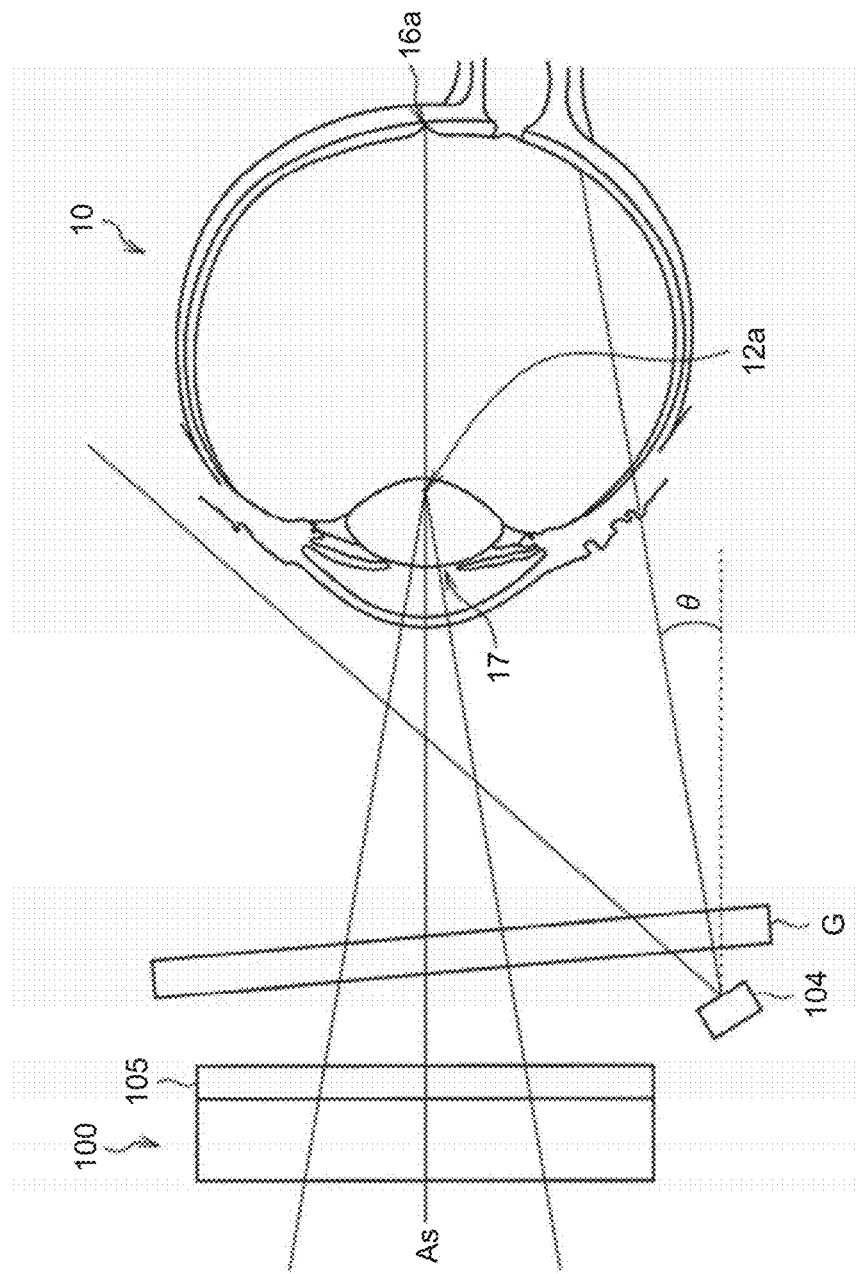
FIG. 15 is a schematic side view illustrating the positional relation between the eyeball 10 of the user and an information processing device 200 when the information processing device according to a second embodiment of the present disclosure is mounted.

FIG. 15 is a schematic side view illustrating the positional relation between the eyeball 10 of the user and the information processing device 200 when the information processing device 200 is mounted on the user. As illustrated in FIG. 15, the information processing device 200 according to the present embodiment further includes a transparent member 105 in addition to the configuration described in the first embodiment. The transparent member 105 is disposed on the user eyeball 10 side in the information processing device 200.

The transparent member 105 according to the present embodiment is formed of a transparent material such as glass or acrylic resin. Thus, the user can visually recognize various kinds of visual information displayed on the display unit (not illustrated) of the information processing device 200 through the transparent member 105.

Figure 16:
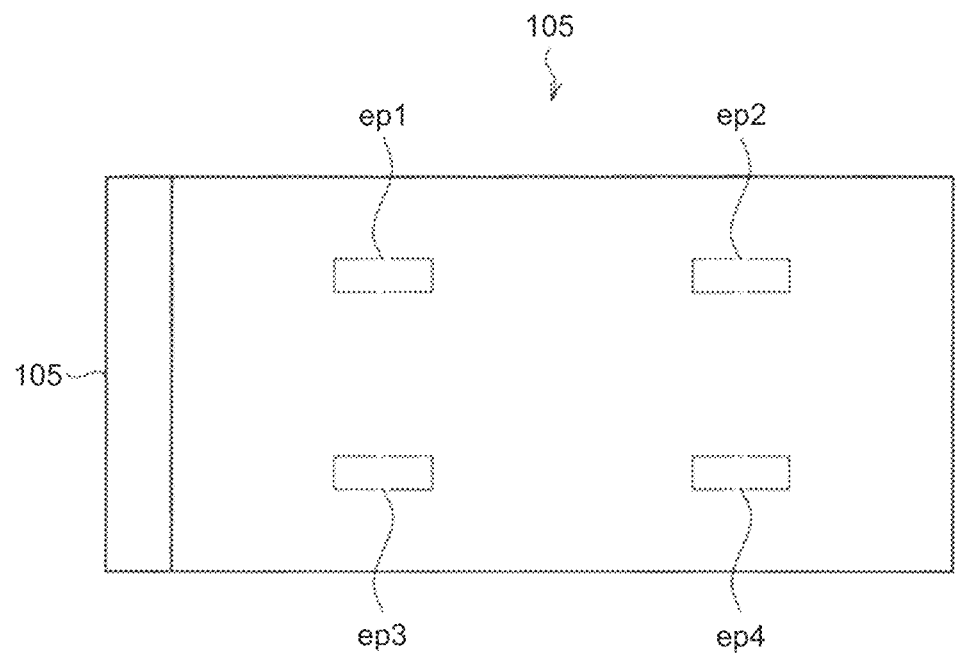
FIG. 16 is a front view of a transparent member according to the embodiment when viewed from the user side.

FIG. 16 is a front view of the transparent member 105 according to the present embodiment when viewed from the user side. As illustrated in FIG. 16, the transparent member 105 according to the present embodiment may be formed in, for example, a plate shape. It is one characteristic of the transparent member 105 according to the present embodiment to include a plurality of light emission points ep each configured to irradiate an eye of the user with light guided from a light source.

To assure the accuracy of the sight line detection by the pupil cornea reflection method, at least two bright spots are preferably detected on the cornea, and the detection accuracy tends to improve as the number of detected bright spots increases. Thus, the transparent member 105 according to the present embodiment may include at least two light emission points ep, and the two light emission points ep may be disposed at positions where the light emission points ep can form two bright spots on the cornea of each of the eyes. FIG. 16 illustrates an example in which the transparent member 105 includes four light emission points ep1 to ep4. As illustrated in FIG. 15, an image capturing unit 104 according to the present embodiment is disposed at a position where the image capturing unit 104 can capture an image of at least two bright spots on the cornea.

Figure 17:
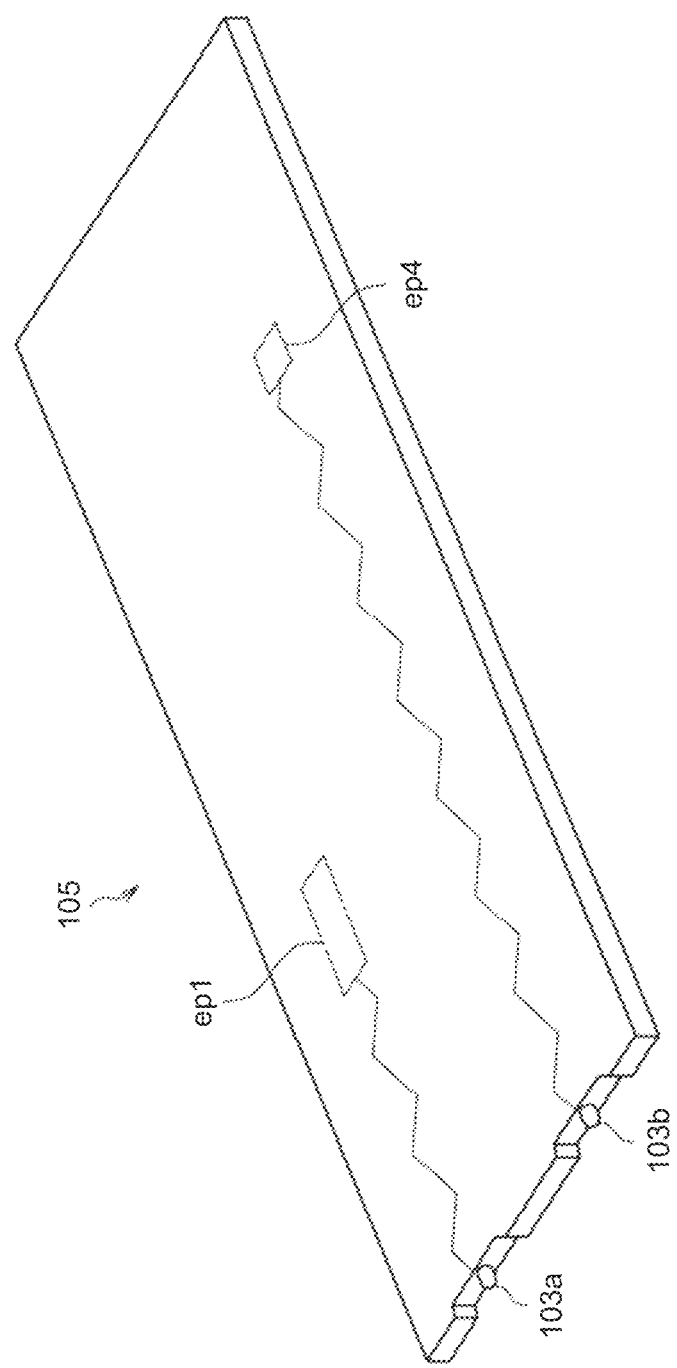
FIG. 17 is a perspective view illustrating a structural characteristic of the transparent member according to the embodiment.

The following describes each light emission point ep according to the present embodiment in more detail with reference to FIG. 17. FIG. 17 is a perspective view illustrating a structural characteristic of the transparent member 105 according to the present embodiment. As described above, the light emission point ep according to the present embodiment functions to irradiate an eye of the user with light guided from the light source. In this case, the light emission point ep may achieve, through reflection inside the transparent member 105, the guiding of light emitted from a light source 103 disposed at a side part of the transparent member 105 as illustrated in FIG. 17. FIG. 17 illustrates an example in which light from a light source 103*a* is guided to the light emission point ep1 and light from a light source 103*b* is guided to the light emission point ep4.

Each light emission point ep as described above may be formed by, for example, cutout fabrication. With the cutout fabrication, a light emission point in an optional shape can be formed at an optional place on the transparent member 105 at low cost. As described above, a larger number of bright spots are desirably detected on the cornea to assure the accuracy of the sight line detection by the pupil cornea reflection method. However, typically in the conventional method, one light source forms one bright spot, and thus the number of light sources needs to be physically increased to detect a large number of bright spots on the cornea. In the present embodiment, a plurality of transparent members 105 are placed over one another to control the light emission intensity of the light source 103 and perform switching of light emission from a plurality of light emission points ep, and thus it is possible to significantly reduce cost of the light source 103 and use different bright spots for each user.

Each light emission point ep according to the present embodiment may be formed by a method other than the cutout fabrication. For example, the light emission point ep may be formed by differentiating the reflectance of an optional place from those of surroundings. For example, the reflectance may be differentiated by using, at the formation place of the light emission point ep, a material different from that of surroundings, or by adding an alternative member to the formation place of the light emission point ep.

When a plurality of bright spots are formed on the cornea, the bright spots need to be distinguishable from each other in terms of the direction of emitted light to which each bright spot is attributable. Thus, typically in the conventional method, disposition of a plurality of light sources is adjusted to specify to which light source each bright spot is attributable. However, each light emission point ep according to the present embodiment can be formed in an optional shape. Thus, in the present embodiment, the plurality of light emission points ep1 and ep4 can be formed in light emission shapes different from each other as illustrated in FIG. 17, in other words, the shapes of bright spots can be differentiated so that the bright spots can be easily distinguished from each other.

Figure 18:
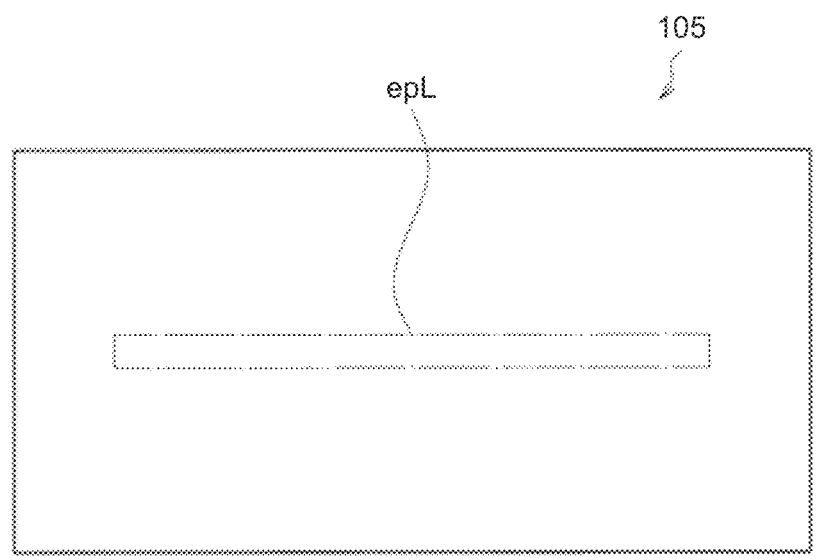
FIG. 18 is a diagram illustrating a linear light emission point according to the embodiment.
Figure 19:
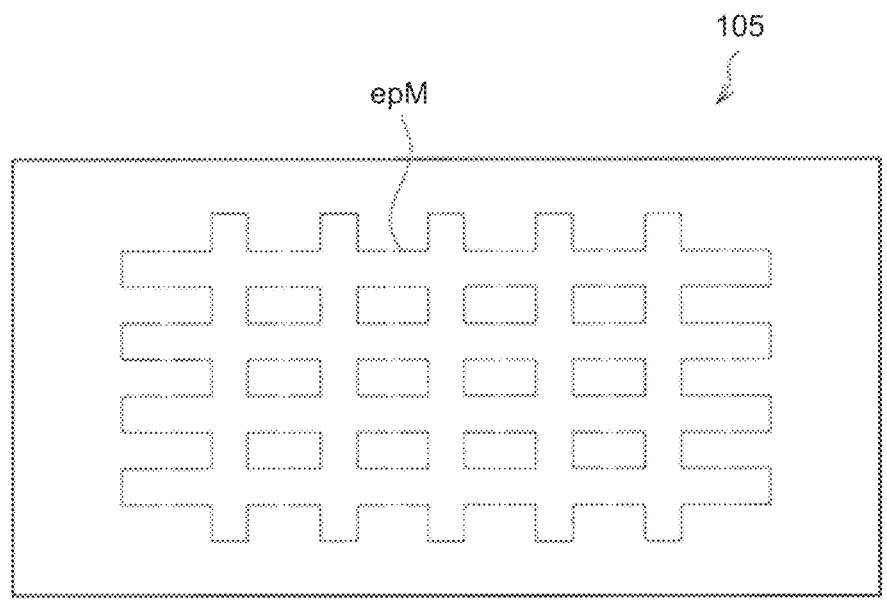
FIG. 19 is a diagram illustrating a mesh light emission point according to the embodiment.

The light emission point ep according to the present embodiment may be formed in a linear shape or a mesh shape. FIG. 18 is a diagram illustrating a light emission point epL linear according to the present embodiment, and FIG. 19 is a diagram illustrating a mesh light emission point epM according to the present embodiment. When the linear light emission point epL or the mesh light emission point epM is used, for example, irregularities of the eyeball surface can be analyzed in detail by observing a corresponding reflection image, and thus the sight line detection can be achieved at higher accuracy.

The transparent member 105 according to the present embodiment may be formed integrally with, for example, the display unit. Thus, with the transparent member 105 according to the present embodiment, the size and weight of the information processing device 200 can be further reduced.

Figure 20:
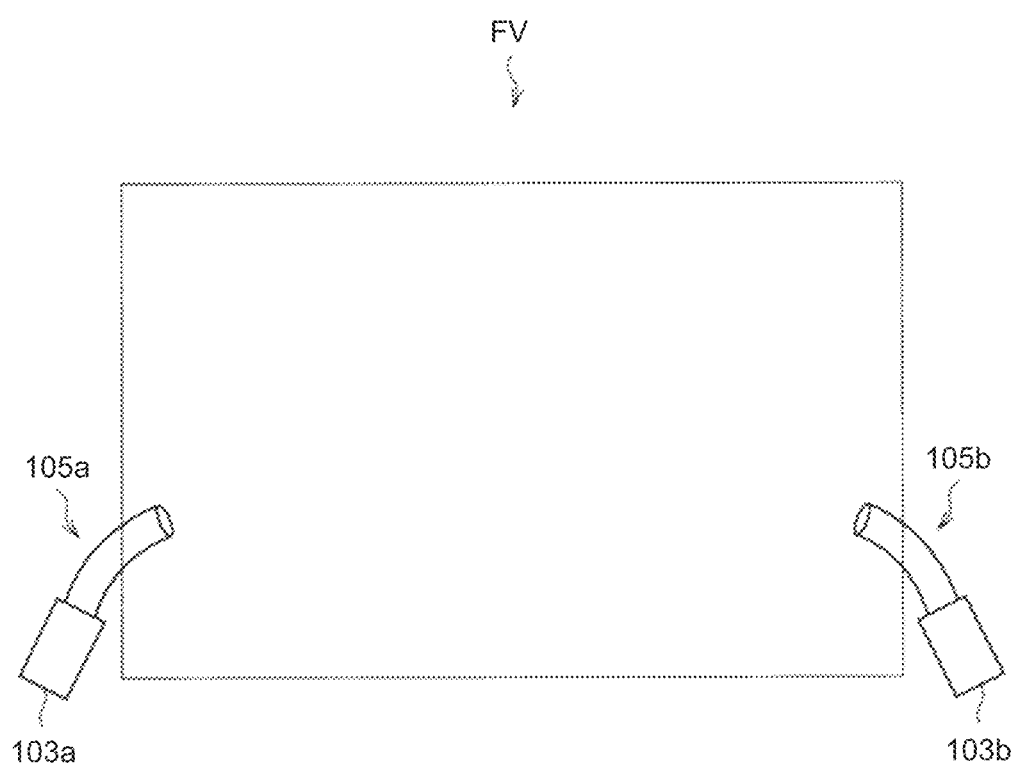
FIG. 20 is a diagram for describing the transparent member having a bar shape according to the embodiment.

The above description is made on the example in which the transparent member 105 according to the present embodiment is formed in a plate shape, but the shape of the transparent member 105 according to the present embodiment is not limited to such an example. The transparent member 105 according to the present embodiment may be achieved by, for example, a member having a bar shape. FIG. 20 is a diagram for describing a transparent member having a bar shape according to the present embodiment. FIG. 20 illustrates the visual field of the user FV and two transparent members 105*a* and 105*b* each having a bar shape. In this case, the two transparent members 105*a* and 105*b* each having a bar shape can irradiate the eyes of the user with light guided from the light sources 103*a* and 103*b*, respectively, disposed outside the visual field FV.

The characteristics of the transparent member 105 and the light emission points ep according to the present embodiment are described in detail above. With the transparent member 105 and the light emission points ep according to the present embodiment, light guided from the light source 103 disposed outside the visual field of the user can be emitted from an optional place, for example, near the center of the visual field. In addition, as described above, each light emission point ep according to the present embodiment can be formed in an optional shape, and thus the accuracy of the sight line detection can be effectively improved by forming the light emission point ep in various kinds of shapes in accordance with usage. Moreover, the light emission point ep according to the present embodiment can be formed stably in a large amount by pressing or the like, and thus reduced manufacturing cost and high position accuracy as compared to that of light source attachment can be expected.

The transparent member 105 according to the present embodiment may be used together with direct irradiation from the light source 103. In addition, the information processing device 200 may perform various kinds of control of the light emission points ep and the light source 103. For example, in a situation in which the environment is dark, the information processing device 200 may perform, for example, control to reduce electric power consumption by reducing the light emission intensity of the light source 103 or limiting the number of light emission points ep in use. The configuration and function of the information processing device 200 according to the present embodiment can be flexibly modified in accordance with specifications and operations.

The transparent member 105 according to the present embodiment is also applicable to an information processing device that does not perform the arithmetic processing in the embodiments of the present disclosure. In other words, the transparent member 105 can be regarded as a component independent from the arithmetic processing in the embodiments of the present disclosure. It should be noted that, when the transparent member 105 according to the present embodiment is applied, the sight line detection at higher accuracy than that of a typical hardware configuration is provided, and as a result, at least some of problems of the typical hardware configuration can be solved.

3. EXEMPLARY HARDWARE CONFIGURATION

Figure 21:
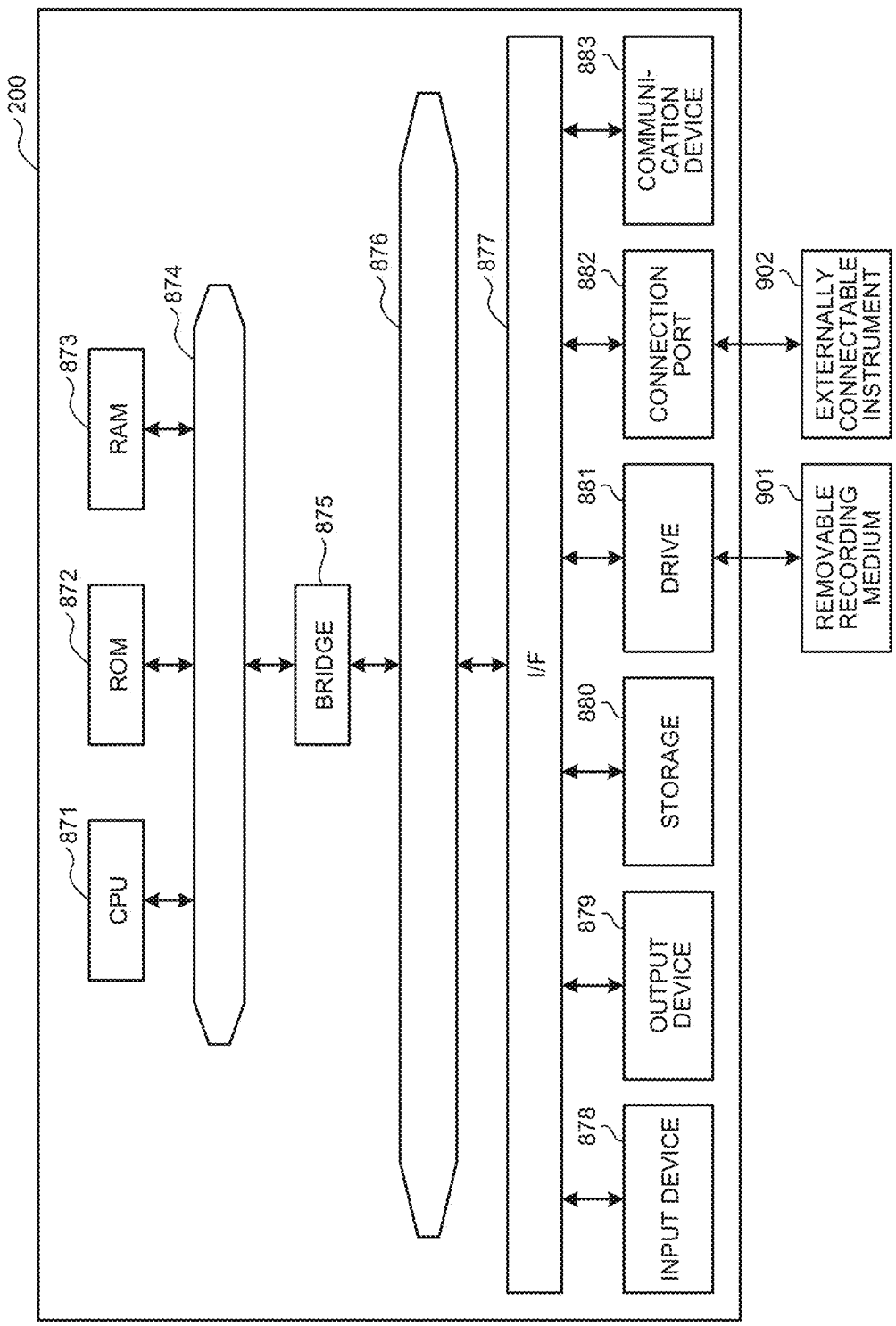
FIG. 21 is a diagram illustrating an exemplary hardware configuration of the information processing device according to an embodiment of the present disclosure.

The following describes an exemplary hardware configuration of the information processing device 200 according to an embodiment of the present disclosure. FIG. 21 is a block diagram illustrating an exemplary hardware configuration of the information processing device 200 according to the embodiment of the present disclosure. As illustrated in FIG. 21, the information processing device 200 includes, for example, a CPU 871, a ROM 872, a RAM 873, a host bus 874, a bridge 875, an external bus 876, an interface 877, an input device 878, an output device 879, a storage 880, a drive 881, a connection port 882, and a communication device 883. The above-described hardware configuration is exemplary, and some of the components may be omitted. Any component other than the components described above may be further provided.

(CPU 871)

The CPU 871 functions as, for example, an arithmetic processing device or a control device, and controls the entire operation of each component or part thereof based on various computer programs recorded in the ROM 872, the RAM 873, the storage 880, or a removable recording medium 901.

(ROM 872 and RAM 873)

The ROM 872 stores a computer program to be read by the CPU 871, data to be used in calculation, and the like. The RAM 873 temporarily or permanently stores, for example, a computer program to be read by the CPU 871, and various parameters and the like that change as appropriate when the computer program is executed.

(Host Bus 874, Bridge 875, External Bus 876, and Interface 877)

For example, the CPU 871, the ROM 872, and the RAM 873 are connected with one another through the host bus 874 through which fast data transmission is possible. For example, the host bus 874 is connected with, through the bridge 875, the external bus 876 through which data transmission is performed at relatively low speed. The external bus 876 is connected with various kinds of components through the interface 877.

(Input Device 878)

The input device 878 is achieved by, for example, a mouse, a keyboard, a touch panel, a button, a switch, or a lever. Alternatively, the input device 878 is sometimes achieved by a remote controller capable of transmitting a control signal by using infrared or other radio wave. The input device 878 includes a voice input device such as a microphone.

(Output Device 879)

The output device 879 is a device capable of visually or audibly notifying acquired information to the user, such as a display device such as cathode ray tube (CRT), LCD, or organic EL, an audio output device such as a speaker or a headphone, a printer, a cellular phone, or a facsimile. The output device 879 according to the present disclosure includes various kinds of vibration devices capable of outputting haptic impulsion.

(Storage 880)

The storage 880 is a device for storing various kinds of data. Examples of the storage 880 include a magnetic storage device such as a hard disk drive (HDD), a semiconductor storage device, an optical storage device, and a magneto-optical storage device.

(Drive 881)

The drive 881 is a device, such as a magnetic disk, an optical disk, a magneto optical disc, or a semiconductor memory, which reads information recorded on the removable recording medium 901 or writes information to the removable recording medium 901.

(Removable Recording Medium 901) The removable recording medium 901 is, for example, a DVD media, a Blu-ray (registered trademark) media, a HD DVD media, or one of various semiconductor storage medium. The removable recording medium 901 may be, for example, an IC card on which a non-contact IC chip is mounted, or an electronic device.

(Connection Port 882)

The connection port 882 is, for example, a universal serial bus (USB) port, an IEEE1394 port, a small computer system interface (SCSI), a RS-232C port, or a port for connecting an externally connectable instrument 902 such as an optical audio terminal.

(Externally Connectable Instrument 902)

The externally connectable instrument 902 is, for example, a printer, a portable music player, a digital camera, a digital video camera, or an IC recorder.

(Communication Device 883)

The communication device 883 is a communication device for connecting to a network, and is, for example, a wired or wireless LAN, Bluetooth (registered trademark), or wireless USB (WUSB) communication card, an optical communication router, an asymmetric digital subscriber line (ADSL) router, or one of various communication modems.

4. CONCLUSION

As described above, the information processing device 200 according to the embodiment of the present disclosure can determine calibration executability for each eye and use only the sight line data of an eye for which calibration is determined to be executable, when executing calibration for the eye. With this configuration, it is possible to perform sight line detection at higher accuracy by removing influence of one of the eyes that could cause accuracy decrease.

The preferable embodiments of the present disclosure are described above in detail with reference to the accompanying drawings, but the technical scope of the present disclosure is not limited to such examples. Various changes and modifications could be thought of by any person having typical knowledge in the technical field of the present disclosure within the range of the technical idea recited in the claims, and it should be understood that these changes and modifications belong to the technical scope of the present disclosure.

Effects described in the present specification are merely explanatory or exemplary but not restrictive. Thus, the technology according to the present disclosure achieves, together with or in place of the above-described effects, any other effect that is clear to the skilled person in the art from description of the present specification.

In addition, a computer program for causing hardware such as a CPU, a ROM, and a RAM built in a computer to achieve a function equivalent to that of any component included in the information processing device 200 may be produced, and a computer-readable recording medium in which the computer program is recorded may be provided.

The steps of each processing performed by the information processing device 200 in the present specification do not necessarily need to be processed in a temporally sequential manner in the order written in the corresponding flowchart. For example, the steps of each processing performed by the information processing device 200 may be processed in an order different from the order written in the corresponding flowchart, or may be processed in parallel.

Configurations as described below belong to the technical scope of the present disclosure.

(1)

An information processing device comprising an arithmetic processing unit configured to execute arithmetic processing related to calibration of detection of a sight line toward a display unit, wherein the arithmetic processing unit determines calibration executability for each of both eyes based on acquired sight line data and uses only the sight line data of an eye for which calibration is determined to be executable when executing calibration for the eye.

(2)
The information processing device according to (1), wherein the arithmetic processing unit determines the calibration executability for each of both eyes based on usable calibration points.

(3)
The information processing device according to (2), wherein the arithmetic processing unit determines that calibration is inexecutable for an eye when the number of usable calibration points is smaller than a threshold.

(4)
The information processing device according to any one of (1) to (3), wherein the arithmetic processing unit determines the calibration executability for each of both eyes based on variance of an optical axis vector at all usable calibration points.

(5)
The information processing device according to (4), wherein the arithmetic processing unit determines that calibration is inexecutable for an eye when a correlation coefficient indicating a correlation relation between the optical axis vector and a marker vector from a pupil center of a user to one of the calibration points at which a gaze point marker is displayed is smaller than a threshold.

(6)
The information processing device according to any one of (2) to (5), wherein the arithmetic processing unit determines usability of a calibration point based on the sight line data accumulated at the calibration point.

(7)
The information processing device according to any one of (2) to (6), wherein the arithmetic processing unit determines that a calibration point is unusable when the number of pieces of the sight line data accumulated at the calibration point does not exceed a predetermined number in a predetermined time.

(8)
The information processing device according to any one of (1) to (7), wherein the arithmetic processing unit calculates an optical axis vector by a pupil cornea reflection method based on a captured image including an eye of a user and obtained by image capturing when the eye of the user is irradiated with light from a light source and a gaze point marker is displayed at a calibration point.

(9)
The information processing device according to any one of (1) to (8), further comprising a display control unit configured to control a display position of an object displayed on the display unit in accordance with an eye for which the calibration has been executed.

(10)
The information processing device according to (9), wherein the display control unit displays the object in an area corresponding to an eye for which the calibration has been executed.

(11)
The information processing device according to (10), wherein the display control unit displays the object in a calibration area for an eye for which the calibration has been executed.

(12)
The information processing device according to any one of (1) to (11), further comprising an evaluation unit configured to evaluate optical axis vector variance calculated for a plurality of calibration points.

(13)
The information processing device according to any one of (1) to (12), further comprising a marker control unit configured to change a display position of a gaze point marker displayed by the display unit.

(14)
The information processing device according to any one of (1) to (13), further comprising a transparent member including at least two light emission points each configured to irradiate an eye of a user with light guided from a light source, wherein the at least two light emission points are disposed at positions where the at least two light emission points can form at least two bright spots on the cornea of each of both eyes.

(15)
The information processing device according to (14), wherein the transparent member is formed in a plate shape and disposed between each eye of the user and the display unit.

(16)
The information processing device according to (14) or (15), wherein the light emission point is formed by cutout fabrication.

(17)
The information processing device according to any one of (14) to (16), wherein the at least two light emission points have light emission shapes different from each other.

(18)
The information processing device according to any one of (14) to (17), further comprising an image capturing unit configured to capture an image including an eyeball of the user, wherein the image capturing unit is disposed at a position where the image capturing unit can capture an image of the at least two bright spots on the cornea.

(19)
An information processing method comprising executing, by a processor, arithmetic processing related to calibration of detection of a sight line toward a display unit, wherein the executing arithmetic processing further includes determining calibration executability for each of both eyes based on acquired sight line data and using only the sight line data of an eye for which calibration is determined to be executable when executing calibration for the eye.

(20)
A computer program configured to cause a computer to function as an information processing device comprising an arithmetic processing unit configured to execute arithmetic processing related to calibration of detection of a sight line toward a display unit, wherein the arithmetic processing unit determines calibration executability for each of both eyes based on acquired sight line data and uses only the sight line data of an eye for which calibration is determined to be executable when executing calibration for the eye.

(21)
A sight line detection display device including a transparent member including at least two light emission points each configured to irradiate an eye of a user with light guided from a light source, in which the at least two light emission points are disposed at positions where the at least two light emission points can form at least two bright spots on the cornea of each of both eyes.

(22)
A sight line detection transparent member including at least two light emission points each configured to irradiate an eye of a user with light guided from a light source, in which the at least two light emission points are disposed at positions where the at least two light emission points can form at least two bright spots on the cornea of each of both eyes.

REFERENCE SIGNS LIST 10 eyeball
14 cornea
17 pupil
100 display device
110 light source
120 image capturing unit
130 display unit
140 control unit
150 transmission-reception unit
200 information processing device
210 transmission-reception unit
220 marker control unit
230 arithmetic processing unit
240 storage unit
250 evaluation unit
260 display control unit
105 transparent member

The invention claimed is:

1. An information processing device, comprising:
a marker control unit configured to acquire sight line data;
an arithmetic processing unit configured to execute arithmetic processing related to calibration of detection of a sight line of a user toward a display unit, wherein the arithmetic processing unit is further configured to:
determine calibration executability for each eye of both eyes of the user based on the acquired sight line data,
execute calibration for a first eye of both the eyes of the user, and
use the acquired sight line data of a first eye of both the eyes for which calibration is determined to be executable based on the execution of the calibration of the first eye of both the eyes;
a transparent member including at least two light emission points, wherein
each light emission point of the at least two light emission points is configured to irradiate each eye of both the eyes of the user with light guided from a light source, and
the at least two light emission points are at positions where the at least two light emission points are configured to form at least two bright spots on a cornea of each eye of both the eyes.

2. The information processing device according to claim 1, wherein the arithmetic processing unit is further configured to determine the calibration executability for each eye of both the eyes based on a usable calibration point.

3. The information processing device according to claim 2, wherein the arithmetic processing unit is further configured to determine that the calibration is inexecutable for a second eye of both the eyes based on a number of usable calibration points smaller than a threshold.

4. The information processing device according to claim 2, wherein the arithmetic processing unit is further configured to determine usability of a calibration point based on the sight line data accumulated at the calibration point.

5. The information processing device according to claim 2, wherein the arithmetic processing unit is further configured to determine that a calibration point is unusable based on a number of pieces of the sight line data accumulated at the calibration point does not exceed a specific number in a specific time.

6. The information processing device according to claim 1, wherein the arithmetic processing unit is further configured to determine the calibration executability for each eye of both the eyes based on variance of an optical axis vector at each usable calibration point of a plurality of usable calibration points.

7. The information processing device according to claim 6, wherein
the arithmetic processing unit is further configured to determine that the calibration is inexecutable for a second eye of both the eyes when a correlation coefficient is smaller than a threshold,
the correlation coefficient indicates a correlation relation between the optical axis vector and a marker vector, and
the marker vector is from a pupil center of the user to a usable calibration point of the plurality of usable calibration points at which a gaze point marker is displayed.

8. The information processing device according to claim 1, wherein
the arithmetic processing unit is further configured to calculate an optical axis vector by a pupil cornea reflection method,
the pupil cornea reflection method is based on a captured image including an eye of both the eyes of the user, and
the captured image is obtained by an image capturing operation when the eye of the user is irradiated with the light from the light source and a gaze point marker is displayed at a calibration point.

9. The information processing device according to claim 1, further comprising a display control unit configured to control a display position of an object displayed on the display unit based on the first eye for which the calibration has been executed.

10. The information processing device according to claim 9, wherein the display control unit is further configured to display the object in an area corresponding to an eye of both the eyes of the user for which the calibration has been executed.

11. The information processing device according to claim 10, wherein the display control unit is further configured to display the object in a calibration area for an eye of both the eyes of the user for which the calibration has been executed.

12. The information processing device according to claim 1, further comprising an evaluation unit configured to evaluate a variance of an optical axis vector, wherein the variance is calculated for a plurality of calibration points.

13. The information processing device according to claim 1, wherein the marker control unit is further configured to change a display position of a gaze point marker displayed by the display unit.

14. The information processing device according to claim 1, wherein the transparent member is in a plate shape and is between each eye of the user and the display unit.

15. The information processing device according to claim 1, wherein the light emission point is based on cutout fabrication.

16. The information processing device according to claim 1, wherein the at least two light emission points have light emission shapes different from each other.

17. The information processing device according to claim 1, further comprising an image capturing unit configured to capture a first image including an eyeball of the user, wherein the image capturing unit is at a position where the image capturing unit is further configured to capture a second image of the at least two bright spots on the cornea.

18. An information processing method, comprising:
executing, by a processor,
acquiring sight line data;
arithmetic processing related to calibration of detection of a sight line of a user toward a display unit, wherein the execution of arithmetic processing further includes:
determining calibration executability for each eye of both eyes of the user based on the acquired sight line data,
executing calibration for an eye of both the eyes of the user, and
using the acquired sight line data of the eye of both the eyes for which calibration is determined to be executable when executing calibration for the eye;
irradiating, by at least two light emission points of a transparent member, each eye of both the eyes of the user with light guided from a light source; and
forming, by the at least two emission points, at least two bright spots on a cornea of each eye of both the eyes.

19. A non-transitory computer-readable medium having stored thereon computer-executable instructions, which when executed by a computer, cause the computer to execute operations, the operations comprising:
acquiring sight line data;
executing arithmetic processing related to calibration of detection of a sight line of a user toward a display unit, wherein the execution of arithmetic processing further includes:
determining calibration executability for each eye of both eyes of the user based on the acquired sight line data,
executing calibration for an eye of both eyes of the user, and
using the acquired sight line data of the eye of both the eyes for which calibration is determined to be executable when executing calibration for the eye;
irradiating, by at least two light emission points of a transparent member, each eye of both the eyes of the user with light guided from a light source; and
forming, by the at least two emission points, at least two bright spots on a cornea of each eye of both the eyes.

* * * * *